(12) United States Patent
Silvestrini

(10) Patent No.: US 8,287,592 B2
(45) Date of Patent: *Oct. 16, 2012

(54) OPHTHALMIC DEVICES HAVING A DEGRADATION RESISTANT POLYMER

(75) Inventor: Thomas A. Silvestrini, Alamo, CA (US)

(73) Assignee: AcuFocus, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/152,550

(22) Filed: Jun. 3, 2011

(65) Prior Publication Data

US 2011/0238173 A1 Sep. 29, 2011

Related U.S. Application Data

(63) Continuation of application No. 11/106,043, filed on Apr. 15, 2005, now Pat. No. 7,976,577.

(51) Int. Cl.
  *A61F 2/14* (2006.01)
(52) U.S. Cl. ........................................ 623/5.13
(58) Field of Classification Search .......... 623/4.1–5.13, 623/5.16, 6.11, 6.14, 6.17
  See application file for complete search history.

(56) References Cited

U.S. PATENT DOCUMENTS

| | | |
|---|---|---|
| 564,518 A | 7/1896 | Heilborn |
| 1,206,132 A | 11/1916 | Otte |
| 1,959,915 A | 5/1934 | Guthrie |
| 2,129,305 A | 9/1938 | Feinbloom |
| 2,714,721 A | 8/1955 | Stone, Jr. |
| 3,034,403 A | 5/1962 | Neefe |
| 3,270,099 A | 8/1966 | Camp |
| 3,339,997 A | 9/1967 | Wesley |
| 3,458,870 A | 8/1969 | Stone, Jr. |
| 3,507,566 A | 4/1970 | Knapp |
| 3,578,850 A | 5/1971 | Grant |
| 3,600,098 A | 8/1971 | Mohrman |
| 3,726,587 A | 4/1973 | Kendall |
| 3,794,414 A | 2/1974 | Wesley |
| 3,852,032 A | 12/1974 | Urbach |
| 4,010,496 A | 3/1977 | Neefe |
| 4,073,015 A | 2/1978 | Peyman |

(Continued)

FOREIGN PATENT DOCUMENTS

DE 41 34 320 A1 4/1992

(Continued)

OTHER PUBLICATIONS

Accomodation and acuity under night-driving illumination levels. Arumi et al. Opthal. Physiol. Opt. vol. 17, No. 4, pp. 291-299, 1997.

(Continued)

*Primary Examiner* — William H. Matthews
(74) *Attorney, Agent, or Firm* — Knobbe, Martens, Olson & Bear, LLP

(57) ABSTRACT

Disclosed are ophthalmic devices configured to be implanted in an eye of a patient. In one embodiment, the ophthalmic device includes a mask configured to increase the depth of focus of the patient and comprising a highly fluorinated polymeric material in which the number of carbon-fluorine bonds equals or exceeds the number of carbon-hydrogen bonds in the highly fluorinated polymeric material. The highly fluorinated polymeric material can be resistant to degradation upon exposure to ultraviolet light. The mask further includes an aperture configured to transmit light and a portion configured to be substantially opaque to visible light and to surround at least a portion of the aperture.

19 Claims, 19 Drawing Sheets

U.S. PATENT DOCUMENTS

| | | | |
|---|---|---|---|
| 4,099,529 A | 7/1978 | Peyman | |
| 4,138,191 A | 2/1979 | Peyman | |
| 4,191,195 A | 3/1980 | Miller | |
| 4,272,191 A | 6/1981 | Bergkvist | |
| 4,312,575 A | 1/1982 | Peyman et al. | |
| 4,367,949 A | 1/1983 | Lavering | |
| 4,402,681 A | 9/1983 | Haas et al. | |
| 4,450,593 A | 5/1984 | Poler | |
| 4,485,499 A | 12/1984 | Castleman | |
| 4,528,311 A | 7/1985 | Beard et al. | |
| 4,536,240 A | 8/1985 | Winn | |
| 4,547,914 A | 10/1985 | Castleman | |
| 4,547,915 A | 10/1985 | Castleman | |
| 4,575,915 A | 3/1986 | Clark et al. | |
| 4,576,453 A | 3/1986 | Borowsky | |
| 4,607,617 A | 8/1986 | Choyce | |
| 4,612,012 A | 9/1986 | White | |
| 4,615,702 A | 10/1986 | Koziol et al. | |
| 4,617,023 A | 10/1986 | Peyman | |
| 4,624,669 A | 11/1986 | Grendahl | |
| 4,633,866 A | 1/1987 | Peyman et al. | |
| 4,636,049 A | 1/1987 | Blaker | |
| 4,636,211 A | 1/1987 | Nielson et al. | |
| 4,636,212 A | 1/1987 | Posin et al. | |
| 4,637,697 A | 1/1987 | Freeman | |
| 4,639,105 A | 1/1987 | Neefe | |
| 4,641,934 A | 2/1987 | Freeman | |
| 4,642,112 A | 2/1987 | Freeman | |
| 4,646,720 A | 3/1987 | Peyman | |
| 4,655,774 A | 4/1987 | Choyce | |
| 4,666,446 A | 5/1987 | Koziol et al. | |
| 4,669,834 A | 6/1987 | Richter | |
| 4,674,503 A | 6/1987 | Peyman et al. | |
| 4,676,791 A | 6/1987 | Le Master et al. | |
| 4,685,922 A | 8/1987 | Peyman | |
| 4,701,038 A | 10/1987 | Neefe | |
| 4,702,865 A | 10/1987 | Koziol et al. | |
| 4,704,016 A | 11/1987 | de Carle | |
| 4,710,003 A | 12/1987 | Masuda et al. | |
| 4,713,446 A | 12/1987 | DeVore et al. | |
| 4,715,858 A | 12/1987 | Lindstrom | |
| 4,729,373 A | 3/1988 | Peyman | |
| 4,753,654 A | 6/1988 | Posin et al. | |
| 4,779,973 A | 10/1988 | Miller et al. | |
| 4,785,796 A | 11/1988 | Mattson | |
| 4,799,931 A | 1/1989 | Lindstrom | |
| 4,799,973 A | 1/1989 | Lindstrom | |
| 4,806,382 A | 2/1989 | Goldberg et al. | |
| 4,808,181 A | 2/1989 | Kelman | |
| 4,813,955 A | 3/1989 | Achatz et al. | |
| 4,814,050 A | 3/1989 | McGraw et al. | |
| 4,838,266 A | 6/1989 | Koziol et al. | |
| 4,840,175 A | 6/1989 | Peyman | |
| 4,842,599 A | 6/1989 | Bronstein | |
| 4,863,466 A | 9/1989 | Schlegel | |
| 4,865,601 A | 9/1989 | Caldwell et al. | |
| 4,869,587 A | 9/1989 | Breger | |
| 4,878,910 A | 11/1989 | Koziol et al. | |
| 4,881,954 A | 11/1989 | Bikson et al. | |
| 4,890,913 A | 1/1990 | De Carle | |
| 4,891,043 A | 1/1990 | Zeimer et al. | |
| 4,898,461 A | 2/1990 | Portney | |
| 4,923,297 A | 5/1990 | Arndt | |
| 4,932,970 A | 6/1990 | Portney | |
| 4,955,904 A | 9/1990 | Atebara et al. | |
| 4,958,922 A | 9/1990 | Binh et al. | |
| 4,965,545 A | 10/1990 | Johnson | |
| 4,971,432 A | 11/1990 | Koeniger | |
| 4,976,732 A | 12/1990 | Vorosmarthy | |
| 4,983,181 A | 1/1991 | Civerchia | |
| 4,985,559 A | 1/1991 | Goldberg et al. | |
| 4,990,165 A | 2/1991 | Bikson et al. | |
| 4,994,080 A | 2/1991 | Shepard | |
| 4,997,268 A | 3/1991 | Dauvergne | |
| 5,002,571 A | 3/1991 | O'Donnell, Jr. | |
| 5,013,319 A | 5/1991 | Davis | |
| 5,019,097 A | 5/1991 | Knight et al. | |
| 5,026,393 A | 6/1991 | Mackool | |
| 5,030,230 A | 7/1991 | White | |
| 5,041,133 A | 8/1991 | Sayano et al. | |
| 5,061,914 A | 10/1991 | Busch et al. | |
| 5,067,961 A | 11/1991 | Kelman et al. | |
| 5,076,684 A | 12/1991 | Simpson et al. | |
| 5,089,022 A | 2/1992 | Koester et al. | |
| 5,089,024 A | 2/1992 | Christie et al. | |
| 5,098,443 A | 3/1992 | Parel et al. | |
| 5,098,444 A | 3/1992 | Feaster | |
| 5,104,957 A | 4/1992 | Kelman et al. | |
| 5,108,169 A | 4/1992 | Mandell | |
| 5,108,428 A | 4/1992 | Capecchi et al. | |
| 5,112,350 A | 5/1992 | Civerchia et al. | |
| 5,116,111 A | 5/1992 | Simpson et al. | |
| 5,119,555 A | 6/1992 | Johnson | |
| 5,120,120 A | 6/1992 | Cohen | |
| 5,123,921 A | 6/1992 | Werblin et al. | |
| 5,133,745 A | 7/1992 | Falcetta et al. | |
| 5,149,331 A | 9/1992 | Ferdman et al. | |
| 5,152,789 A | 10/1992 | Willis | |
| 5,160,463 A | 11/1992 | Evans et al. | |
| 5,165,897 A | 11/1992 | Johnson | |
| 5,166,712 A | 11/1992 | Portney | |
| 5,171,318 A | 12/1992 | Gibson et al. | |
| 5,185,152 A | 2/1993 | Peyman | |
| 5,192,316 A | 3/1993 | Ting | |
| 5,192,318 A | 3/1993 | Schneider et al. | |
| 5,196,026 A | 3/1993 | Barrett et al. | |
| 5,219,844 A | 6/1993 | Peyman et al. | |
| 5,225,858 A | 7/1993 | Portney | |
| 5,239,066 A | 8/1993 | Falkow et al. | |
| 5,245,367 A | 9/1993 | Miller et al. | |
| 5,245,738 A | 9/1993 | Johnson | |
| 5,258,412 A | 11/1993 | Peyman et al. | |
| 5,260,727 A | 11/1993 | Oksman et al. | |
| 5,261,997 A | 11/1993 | Inselmann | |
| 5,270,744 A | 12/1993 | Portney | |
| 5,274,404 A | 12/1993 | Michael | |
| 5,282,971 A | 2/1994 | Degen et al. | |
| 5,292,514 A | 3/1994 | Capecchi et al. | |
| 5,296,881 A | 3/1994 | Freeman | |
| 5,300,116 A | 4/1994 | Chirila et al. | |
| 5,302,978 A | 4/1994 | Evans et al. | |
| 5,306,297 A | 4/1994 | Rheinish et al. | |
| 5,310,654 A | 5/1994 | Isberg et al. | |
| 5,312,393 A | 5/1994 | Mastel | |
| 5,314,961 A | 5/1994 | Anton et al. | |
| 5,315,344 A | 5/1994 | Clark et al. | |
| 5,318,047 A | 6/1994 | Davenport et al. | |
| 5,322,649 A | 6/1994 | Rheinish et al. | |
| 5,323,788 A | 6/1994 | Silvestrini et al. | |
| 5,325,880 A | 7/1994 | Johnson et al. | |
| 5,336,261 A | 8/1994 | Barret et al. | |
| 5,346,689 A | 9/1994 | Peyman et al. | |
| 5,354,331 A | 10/1994 | Scharcar | |
| 5,366,499 A | 11/1994 | Py | |
| 5,374,272 A | 12/1994 | Arpa et al. | |
| D354,566 S | 1/1995 | Donahoo | |
| 5,391,201 A | 2/1995 | Barret et al. | |
| 5,401,508 A | 3/1995 | Manesis | |
| 5,405,384 A | 4/1995 | Silvestrini | |
| 5,422,424 A | 6/1995 | Selsted et al. | |
| 5,433,745 A | 7/1995 | Graham et al. | |
| 5,434,630 A | 7/1995 | Bransome | |
| 5,437,274 A | 8/1995 | Khoobehl et al. | |
| 5,458,819 A | 10/1995 | Chirila et al. | |
| 5,474,548 A | 12/1995 | Knopp et al. | |
| 5,476,515 A | 12/1995 | Kelman et al. | |
| 5,480,427 A | 1/1996 | Kelman et al. | |
| 5,489,300 A | 2/1996 | Capecchi et al. | |
| 5,505,723 A | 4/1996 | Muller | |
| 5,516,522 A | 5/1996 | Peyman et al. | |
| 5,522,888 A | 6/1996 | Civerchia | |
| 5,526,178 A | 6/1996 | Goldstein et al. | |
| 5,527,356 A | 6/1996 | Peyman et al. | |
| 5,547,473 A | 8/1996 | Peyman | |
| 5,567,365 A | 10/1996 | Weinschenk, III et al. | |
| 5,571,177 A | 11/1996 | Deacon et al. | |
| 5,579,063 A | 11/1996 | Magnante et al. | |

| Patent No. | Date | Inventor |
|---|---|---|
| 5,599,537 A | 2/1997 | Miller, III et al. |
| 5,605,938 A | 2/1997 | Roufa et al. |
| 5,608,471 A | 3/1997 | Miller |
| 5,610,719 A | 3/1997 | Allen et al. |
| 5,628,794 A | 5/1997 | Lindstrom |
| 5,628,798 A | 5/1997 | Eggleston et al. |
| 5,631,243 A | 5/1997 | Kelman et al. |
| 5,632,773 A | 5/1997 | Graham et al. |
| 5,662,706 A | 9/1997 | Legerton et al. |
| 5,662,908 A | 9/1997 | Falkow et al. |
| 5,672,885 A | 9/1997 | Allen et al. |
| 5,674,724 A | 10/1997 | Miller, III et al. |
| 5,674,736 A | 10/1997 | Miller, III et al. |
| 5,693,092 A | 12/1997 | Silvestrini et al. |
| 5,695,983 A | 12/1997 | Miller et al. |
| 5,697,973 A | 12/1997 | Peyman et al. |
| 5,702,440 A | 12/1997 | Portney |
| 5,713,844 A | 2/1998 | Peyman |
| 5,713,957 A | 2/1998 | Steele et al. |
| 5,719,656 A | 2/1998 | Bowling |
| 5,722,971 A | 3/1998 | Peyman |
| 5,731,196 A | 3/1998 | Miller, III et al. |
| 5,731,862 A | 3/1998 | Winkler |
| 5,733,760 A | 3/1998 | Lu et al. |
| 5,757,458 A | 5/1998 | Miller et al. |
| 5,771,088 A | 6/1998 | Perrott |
| 5,771,742 A | 6/1998 | Bokaie et al. |
| 5,774,202 A | 6/1998 | Abraham et al. |
| 5,782,911 A | 7/1998 | Herrick |
| 5,786,883 A | 7/1998 | Miller et al. |
| 5,800,533 A | 9/1998 | Eggleston et al. |
| 5,806,530 A | 9/1998 | Herrick |
| 5,814,680 A | 9/1998 | Imafuku et al. |
| 5,836,313 A | 11/1998 | Perez et al. |
| 5,840,848 A | 11/1998 | Sturrock et al. |
| 5,846,186 A | 12/1998 | Upsher |
| 5,855,605 A | 1/1999 | Herrick |
| 5,858,980 A | 1/1999 | Weiner et al. |
| 5,861,486 A | 1/1999 | DeVore et al. |
| 5,863,537 A | 1/1999 | Dalliet et al. |
| 5,864,128 A | 1/1999 | Plesko |
| 5,864,378 A | 1/1999 | Portney |
| 5,874,537 A | 2/1999 | Kelman et al. |
| 5,903,099 A | 5/1999 | Johnson et al. |
| 5,905,561 A | 5/1999 | Lee et al. |
| 5,919,185 A | 7/1999 | Peyman |
| 5,929,968 A | 7/1999 | Cotie et al. |
| 5,960,812 A | 10/1999 | Johnson |
| 5,964,748 A | 10/1999 | Peyman |
| 5,964,776 A | 10/1999 | Peyman |
| 5,965,330 A | 10/1999 | Evans et al. |
| 5,980,040 A | 11/1999 | Xu et al. |
| 6,010,901 A | 1/2000 | Miller, III et al. |
| 6,024,447 A | 2/2000 | Portney |
| 6,036,957 A | 3/2000 | Weiner et al. |
| 6,063,073 A | 5/2000 | Peyman |
| 6,083,236 A | 7/2000 | Feingold |
| 6,090,141 A | 7/2000 | Lindstrom |
| 6,096,077 A | 8/2000 | Callahan et al. |
| 6,102,946 A | 8/2000 | Nigam |
| 6,106,552 A | 8/2000 | Lacombe et al. |
| 6,126,286 A | 10/2000 | Portney |
| 6,161,544 A | 12/2000 | DeVore et al. |
| 6,164,282 A | 12/2000 | Gwon et al. |
| 6,176,878 B1 | 1/2001 | Gwon et al. |
| 6,183,498 B1 | 2/2001 | DeVore et al. |
| 6,197,019 B1 | 3/2001 | Peyman |
| 6,197,057 B1 | 3/2001 | Peyman et al. |
| 6,197,934 B1 | 3/2001 | DeVore et al. |
| 6,203,538 B1 | 3/2001 | Peyman |
| 6,204,365 B1 | 3/2001 | DeVore et al. |
| 6,210,005 B1 | 4/2001 | Portney |
| 6,217,571 B1 | 4/2001 | Peyman |
| 6,221,067 B1 | 4/2001 | Peyman |
| 6,221,105 B1 | 4/2001 | Portney |
| 6,251,118 B1 | 6/2001 | Proudfoot et al. |
| 6,277,146 B1 | 8/2001 | Peyman et al. |
| 6,280,470 B1 | 8/2001 | Peyman |
| 6,280,471 B1 | 8/2001 | Peyman |
| 6,283,595 B1 | 9/2001 | Breger |
| 6,335,006 B1 | 1/2002 | Miller |
| 6,357,875 B1 | 3/2002 | Herrick |
| 6,358,280 B1 | 3/2002 | Herrick |
| 6,361,560 B1 | 3/2002 | Nigam |
| 6,387,379 B1 | 5/2002 | Goldberg et al. |
| 6,391,055 B1 | 5/2002 | Ikada et al. |
| 6,403,947 B1 | 6/2002 | Hoyt et al. |
| 6,406,494 B1 | 6/2002 | Laguette et al. |
| 6,423,093 B1 | 7/2002 | Hicks et al. |
| 6,425,917 B1 | 7/2002 | Blake |
| 6,436,092 B1 | 8/2002 | Peyman |
| 6,457,826 B1 | 10/2002 | Lett |
| 6,458,141 B1 | 10/2002 | Peyman |
| 6,470,108 B1 | 10/2002 | Johnson |
| 6,488,707 B1 | 12/2002 | Callahan et al. |
| 6,494,910 B1 | 12/2002 | Ganem et al. |
| 6,503,276 B2 | 1/2003 | Lang et al. |
| 6,527,389 B2 | 3/2003 | Portney |
| 6,533,905 B2 | 3/2003 | Johnson et al. |
| 6,536,899 B1 | 3/2003 | Fiala |
| 6,551,307 B2 | 4/2003 | Peyman |
| 6,554,424 B1 | 4/2003 | Miller et al. |
| 6,555,103 B2 * | 4/2003 | Leukel et al. .............. 424/78.04 |
| 6,569,199 B1 | 5/2003 | Dotan et al. |
| RE38,193 E | 7/2003 | Bowling |
| 6,588,022 B1 | 7/2003 | Anders et al. |
| 6,588,902 B2 | 7/2003 | Isogai |
| 6,589,280 B1 | 7/2003 | Koziol |
| 6,592,621 B1 | 7/2003 | Domino |
| 6,599,305 B1 | 7/2003 | Feingold |
| 6,607,556 B1 | 8/2003 | Nigam |
| 6,613,088 B1 | 9/2003 | Babizhayev |
| 6,614,570 B2 | 9/2003 | Johnson et al. |
| 6,620,634 B2 | 9/2003 | Johnson et al. |
| 6,623,497 B1 | 9/2003 | Feingold |
| 6,623,522 B2 | 9/2003 | Nigam |
| 6,624,730 B2 | 9/2003 | Johnson et al. |
| 6,626,941 B2 | 9/2003 | Nigam |
| 6,632,244 B1 | 10/2003 | Nigam |
| 6,663,668 B1 | 12/2003 | Chaouk et al. |
| 6,669,795 B2 | 12/2003 | Johnson et al. |
| 6,673,112 B2 | 1/2004 | Nigam |
| 6,729,599 B2 | 5/2004 | Johnson |
| 6,740,116 B2 | 5/2004 | Morcher |
| 6,742,761 B2 | 6/2004 | Johnson et al. |
| 6,746,890 B2 | 6/2004 | Gupta et al. |
| 6,755,858 B1 | 6/2004 | White |
| 6,786,926 B2 | 9/2004 | Peyman |
| 6,790,298 B2 | 9/2004 | Johnson et al. |
| 6,811,256 B1 | 11/2004 | Becherer et al. |
| 6,849,090 B2 | 2/2005 | Nigam |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,966,648 B2 | 11/2005 | Miller et al. |
| 6,976,997 B2 | 12/2005 | Noolandi et al. |
| 7,025,455 B2 | 4/2006 | Roffman |
| 7,207,998 B2 | 4/2007 | Feingold |
| 7,364,674 B1 | 4/2008 | Hoover |
| 7,404,637 B2 | 7/2008 | Miller et al. |
| 7,404,638 B2 | 7/2008 | Miller et al. |
| 7,462,194 B1 | 12/2008 | Blake |
| 7,491,350 B2 | 2/2009 | Silvestrini |
| 7,628,810 B2 | 12/2009 | Christie et al. |
| 7,645,299 B2 | 1/2010 | Koziol |
| 7,828,844 B2 | 11/2010 | Marmo et al. |
| 2001/0004702 A1 | 6/2001 | Peyman |
| 2001/0027314 A1 | 10/2001 | Peyman |
| 2001/0034516 A1 | 10/2001 | Peyman |
| 2001/0047203 A1 | 11/2001 | Dalton et al. |
| 2001/0050750 A1 | 12/2001 | Breger |
| 2002/0010510 A1 | 1/2002 | Silvestrini |
| 2002/0028330 A1 | 3/2002 | Patel et al. |
| 2002/0055753 A1 | 5/2002 | Silvestrini |
| 2002/0057148 A1 | 5/2002 | Johnson et al. |
| 2002/0075447 A1 | 6/2002 | Andino et al. |
| 2002/0107337 A1 | 8/2002 | Rosenzweig et al. |

| | | |
|---|---|---|
| 2002/0107566 A1 | 8/2002 | Nigam |
| 2002/0111677 A1 | 8/2002 | Nigam |
| 2002/0128710 A1 | 9/2002 | Eggleston |
| 2002/0167640 A1 | 11/2002 | Francis et al. |
| 2002/0173846 A1 | 11/2002 | Blake et al. |
| 2002/0188351 A1 | 12/2002 | Laguette |
| 2002/0196409 A1 | 12/2002 | Jani |
| 2003/0002994 A1 | 1/2003 | Johnson et al. |
| 2003/0007122 A1 | 1/2003 | Streibig |
| 2003/0014042 A1 | 1/2003 | Juhasz et al. |
| 2003/0014107 A1 | 1/2003 | Reynard |
| 2003/0033013 A1 | 2/2003 | Callahan et al. |
| 2003/0045930 A1 | 3/2003 | Nguyen |
| 2003/0055497 A1 | 3/2003 | Hicks et al. |
| 2003/0071893 A1 | 4/2003 | Miller et al. |
| 2003/0078655 A1 | 4/2003 | Callahan et al. |
| 2003/0088313 A1 | 5/2003 | Nigam |
| 2003/0093083 A1 | 5/2003 | Peyman |
| 2003/0105521 A1 | 6/2003 | Perez |
| 2003/0127318 A1 | 7/2003 | Johnson et al. |
| 2003/0142268 A1 | 7/2003 | Miller et al. |
| 2003/0220653 A1 | 11/2003 | Perez |
| 2004/0014253 A1 | 1/2004 | Gupta et al. |
| 2004/0015234 A1 | 1/2004 | Peyman |
| 2004/0019379 A1 | 1/2004 | Glick et al. |
| 2004/0047014 A1 | 3/2004 | Parker et al. |
| 2004/0068317 A1 | 4/2004 | Knight |
| 2004/0078075 A1 | 4/2004 | Koziol |
| 2004/0080239 A1 | 4/2004 | Gupta et al. |
| 2004/0114102 A1 | 6/2004 | Miller et al. |
| 2005/0027355 A1 | 2/2005 | Murakami |
| 2005/0031697 A1 | 2/2005 | Vehige et al. |
| 2005/0033420 A1* | 2/2005 | Christie et al. ............ 623/5.12 |
| 2005/0046794 A1 | 3/2005 | Silvestrini et al. |
| 2005/0049621 A1 | 3/2005 | Feingold et al. |
| 2005/0080485 A1 | 4/2005 | Nigam |
| 2005/0119738 A1 | 6/2005 | Nigam |
| 2005/0143812 A1 | 6/2005 | Paul et al. |
| 2005/0182488 A1 | 8/2005 | Peyman |
| 2005/0187621 A1 | 8/2005 | Brady |
| 2005/0228376 A1 | 10/2005 | Vannoy |
| 2005/0246019 A1 | 11/2005 | Blake et al. |
| 2006/0079959 A1 | 4/2006 | Christie et al. |
| 2006/0079960 A1 | 4/2006 | Christie et al. |
| 2006/0113054 A1 | 6/2006 | Silvestrini |
| 2006/0118263 A1 | 6/2006 | Silvestrini |
| 2006/0203192 A1 | 9/2006 | Miller et al. |
| 2006/0235514 A1 | 10/2006 | Silvestrini |
| 2006/0241751 A1 | 10/2006 | Marmo et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271027 A1 | 11/2006 | Silvestrini et al. |
| 2006/0271176 A1 | 11/2006 | Christie et al. |
| 2006/0271177 A1 | 11/2006 | Christie et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2006/0274267 A1 | 12/2006 | Miller et al. |
| 2007/0225691 A1 | 9/2007 | Silvestrini et al. |
| 2008/0033546 A1 | 2/2008 | Liang |
| 2008/0125862 A1 | 5/2008 | Blake |
| 2008/0151183 A1 | 6/2008 | Altmann |
| 2009/0021692 A1 | 1/2009 | Miller et al. |
| 2009/0059168 A1 | 3/2009 | Miller et al. |
| 2009/0222086 A1 | 9/2009 | Lui et al. |
| 2009/0306773 A1 | 12/2009 | Silversrini et al. |
| 2011/0040376 A1 | 2/2011 | Christie et al. |

FOREIGN PATENT DOCUMENTS

| | | |
|---|---|---|
| EP | 0286433 | 10/1988 |
| EP | 0 457 553 A2 | 11/1991 |
| FR | 369 993 | 1/1907 |
| FR | 2599156 | 5/1988 |
| FR | 2649605 | 1/1991 |
| GB | 1 026 839 | 4/1966 |
| GB | 1276003 | 6/1972 |
| JP | 62167343 A | 7/1987 |
| JP | 64-002644 | 1/1989 |
| JP | 03-001857 | 1/1991 |
| JP | 04-158859 | 6/1992 |
| JP | 6-502782 | 3/1994 |
| JP | 6-509731 | 11/1994 |
| JP | 07-178125 | 7/1995 |
| JP | 07-265340 | 10/1995 |
| JP | 08-103457 | 4/1996 |
| JP | 2004-538034 | 12/2004 |
| SU | 1380743 A1 | 3/1998 |
| WO | WO 87/05797 | 10/1987 |
| WO | WO 92/05694 | 4/1992 |
| WO | WO 93/03776 | 3/1993 |
| WO | WO 94/01058 | 1/1994 |
| WO | WO 94/05232 | 3/1994 |
| WO | WO 94/23327 | 10/1994 |
| WO | WO 95/02356 | 1/1995 |
| WO | WO 95/08135 | 3/1995 |
| WO | WO 96/35397 | 11/1996 |
| WO | WO 97/48004 | 12/1997 |
| WO | WO 97/48005 | 12/1997 |
| WO | WO 98/27896 | 7/1998 |
| WO | WO 99/07309 | 2/1999 |
| WO | WO 00/52516 A2 | 9/2000 |
| WO | WO 00/52516 A3 | 1/2001 |
| WO | WO 01/10641 A | 2/2001 |
| WO | WO 01/87189 | 11/2001 |
| WO | WO 02/13881 | 2/2002 |
| WO | WO 02/27388 | 4/2002 |
| WO | WO 02/102241 A2 | 12/2002 |
| WO | WO 03/030763 A1 | 4/2003 |
| WO | WO 2004/014969 | 2/2004 |
| WO | WO 2004/050132 | 6/2004 |
| WO | WO 2004/105588 A2 | 12/2004 |
| WO | WO 2006/047698 | 5/2006 |
| WO | WO 2008/036671 | 3/2008 |

OTHER PUBLICATIONS

Accommodation and Presbyopia. Croft et al., International Opthalmology Clinics: Spring 2001, vol. 41, Issue 2, pp. 33-46.

Accomodation dynamics as a function of age. Heron et al. Opthal. Physiol. Opt. 2002 22:389-396.

Accommodation Responses and Ageing. Heron et al. IOVS, Nov. 1999, vol. 40, No. 12, pp. 2872-2883.

Accommodative responses to anisoaccommodative targets. Koh et al. Ophthal. Physiol. Opt. vol. 18, No. 3, pp. 254-262, 1998.

Accommodation responses to flickering stimuli. Chauhan et al. Ophthal. Physiol. Opt. vol. 16. No. 5, pp. 391-408, 1996.

Accommodation to perceived depth in stereo tests. Koh et al. Ophthal. Physiol. Opt. vol. 18, No. 3, pp. 279-284, 1998.

Age Changes in the Interactions between the Accommodation and Vergence Systems. Heron et al. Optometry and Vision Science. vol. 78, No. 10, Oct. 2001.

Anterior Ciliary Sclerotomy for Treatment of Presbyopia: A Prospective Controlled Study. Hamilton et al. Ophthalmology, vol. 109, No. 11: Nov. 2002: pp. 1970-1977.

Can Accommodation be Surgically Restored in Human Presbyopia? Glasser, Adrian. Optometry and Vision Science, vol. 76, No. 9, Sep. 1999.

Changes in the static accommodation response with age. Kalsi et al. Ophthal. Physiol. Opt. vol. 21, No. 1, pp. 77-84, 2001.

Choice of Spatial Frequency for Contrast Sensitivity Evaluation After Corneal Refractive Surgery. Montes-Mico et al. Journal of Refractive Surgery, vol. 17: Nov./Dec. 2001: pp. 646-651.

Choyce, P. "Implants with Coloured and Opaque Portions: Implants with Built-In Stenopeic Aperture," pp. 21-26 "Uniocular Aphakia Corrected by Anterior Chamber Implants with Built-In Stenipeic Aperture," pp. 132-136, 1964.

Clinical Characteristics of Lamellar Channel Deposits After Implementation of Intacs. Ruckhofer et al. J Cataract Refract Surg, vol. 26, Oct. 2000: pp. 1473-1479.

Corneal Topography: The State of the Art, Alignment of Videokeratographs. Mandell et al. Chpt. 2, pp. 17-23, Jan. 1995.

Dynamics of the accommodation response to abrupt changes in target vergence as a function of age. Heron et al. Vision Research 41 (2001) 507-519.

Dynamic retinoscopy and accomodation. Whitefoot et al. Ophthal. Physiol. Opt. vol. 12, Jan. 1992, pp. 8-17.

Eduard Jaeger's Test-Types (Schrift-Scalen) and Historical Development of Vision Tests. Runge, Paul E. Tr. Am. Ophth. Soc. vol. 98, 2000: 375.

Eight Years Experience with Permalens Intracorneal Lenses in Non-human Primates. Werblin et al. Refractive & Corneal Surgery, vol. 8, Jan./Feb. 1992, pp. 12-21.

EP 00 913659.9 Examination Report, dated Jul. 20, 2006, 5 pp.

Errors in determining the direction of the visual axis in the presence of defocus. Atchison et al. Ophthal. Physiol. Opt., vol. 18, No. 5, pp. 463-467, 1998.

Evaluate surgical routine to determine DLK cause, surgeon advises. Piechocki, Michael. Ocular Surgery News: Refractive Surgery, Jan. 1, 2003: p. 14.

Explanation for the observation of isogyres in crystalline lenses viewed between crossed polarizers. Opthal. Physiol. Opt., vol. 13, Apr. 1993, pp. 209-211.

Flap Measurements With the Hansatome Microkeratome. Spadea et al. Journal of Refractive Surgery, vol. 18, Mar./Apr. 2002: pp. 149-154.

Focused and divided attention in stereoscopic deth. Wickens et al. SPIE, vol. 1256 Stereoscopic Displays and Applications (1990); pp. 28-34.

Griffith et al.; "Functional Human Corneal Equivalents Constructed from Cell Lines", Science, vol. 286, Dec. 10, 1999 pp. 2169-2172.

Groppi, J. J. "New Aspects in the Fitting of the Multi-Range Bifocal Contact Lens" Contacto, vol. 15:22-29 1971.

Holes in Clear Lenses Demonstrate a Pinhole Effect. Zacharia et al. Arch Ophthalmol, vol. 106, Apr. 1988, pp. 511-513.

Human Visual System—Image Formation, Encyclopedia of Imaging Science and Technology, Roorda, A., 2002, pp. 539-557.

Hybrid diffractive-refractive achromatic spectacle lenses. Charman, W. N. Opthal. Physiol. Opt., vol. 14, Oct. 1994: pp. 389-392.

Iijima et al. "Formation of a spherical multicellular aggregate (spheroid) of animal cells in the pores of polyurethane foam as a cell culture substratum and its application to a hybrid artificial liver", Polymers for Tissue Engineering , pp. 273-286, VSP 1998.

Imaging in the 21st century. Charman, W. N. Ophthal. Physiol. Opt., vol. 18, No. 2, pp. 210-223, 1998.

Intra-Ocular Lenses and Implants. Choyce, Peter. Chpts.4 & 17, 1964.

Intraocular pressure after excimer laser myopic refractive surgery. Montes-Mico et al. Ophthal. Physiol. Opt., vol. 21, No. 3, pp. 228-235, 2001.

Intrastromal Crystalline Deposits Following Hydrogel Keratophakia in Monkeys. Parks et al. Cornea 12(1): 29-34,1993.

Lipid Deposits Posterior to Impermeable Intracornel Lenses in Rhesus Monkeys: Clinical, Histochemical, and Ultrastructural Studies. Rodrigues et al. Refractive & Corneal Surgery, vol. 6, Jan./Feb. 1990: DO. 32-37.

Mastel Precision: Fiber Optic Ring Illuminator (Product Nos. 3776 & 4050) US Patent No. 5312393 User Manual. Rev: A02: Jan. 11, 1995, pp. 1-25.

Mastel Precision: The Ring Light. http://www.mastel.com/ring_light.html. Jul. 28, 2003.

Measurement of the wave-front aberration of the eye by a fast psychophysical procedure. He et al. J. Opt. Soc. Am. A, vol. 15, No. 9: Sep. 1998, pp. 2449-2455.

Microstructural Changes in Polyester Biotextiles During Implantation in Humans. King et al. NC State University: JTATM, vol. 1, Issue 3, Spring 2001, pp. 1-8.

Miller et al. "Quantification of the Pinhole effect" Perspectives in Refraction, vol. 21:347-350 1977.

Near vision, lags of accommodation and myopia. Charman, W. N. Ophthal. Physiol. Opt., vol. 19, No. 2, pp. 126-133, 1999.

New Visual Acuity Charts for Clinical Research. Ferris et al. American Journal of Ophthalmology, 94: 91-96, 1982.

Night myopia and driving. Charman, W. N. Ophthal. Physiol. Opt., vol. 16, No. 6, p. 474-485, 1996.

Notch in contrast sensitivity function of optical origin: diffraction effects of acrylic filters. Irving et al. Ophthal. Physiol. Opt., vol. 13, Apr. 1993: pp. 179-182.

On modeling the causes of presbyopia. Glasser, A. Vision Research 41(2001) 3083-3087.

On the linearity of accommodation dynamics. Charman, W. N. Vision Research 40 (2000) 2057-2066.

Optical Aspects of Tolerances to Uncorrected Ocular Astigmatism. Charman et al. Optometry and Vision Science, vol. 70, No. 2: pp. 111-117, 1993.

Optical Modeling of Contact Lens Performance Final Report Covering Period Jul. 15, 1994-Mar. 31, 1995. Grivenkamp et al. for Pilkington Barnes Hind, Issued Apr. 5, 1995.

Optometric Clinical Practice Guideline Care of the Patient With Presbyopia: Reference Guide for Clinicians. Mancil et al. Mar. 20, 1998.

PermaVision intracorneallens shows promise for hyperopia. Kronemyer, Bob. Ocular Surgery News: Jan. 1, 2003; p. 8.

Perspectives in Refraction: Quantification of the Pinhole Effect. Miller et al. Survey of Ophthalmology, vol. 21, No. 4, Jan./Feb. 1977, pp. 347-350.

Poly(methyl methacrylate) model study of optical surface quality after excimer laser photo refractive keratectomy. Hauge et al. J Cataract Refract Surg., vol. 27, Dec. 2001, pp. 2026-2035.

Procyon: Marketing Information for Distributors: Pupil Measurement and Refractive Sugery (Samples from Academic Papers 1994 and 2002). pp. 1-17.

Refractive keratoplasty with intrastromal hydrogel lenticular implants. McCarey et al. Invest. Ophthalmol. Vis. ScL, Jul. 1981, pp. 107-115.

Retinal Image Quality in the Human Eye as a Function of the Accommodation. Lopex-Gil et al. Vision Research, vol. 38, No. 19,Jul. 3, 1998, pp. 1-11.

Rosenbloom "The Controlled-Pupil Contact Lens in Low Vision Problems" Journal of the American Optometric Association, pp. 836, 838, 840 1969.

Simple parametric model of the human ocular modulation transfer function, A. Deeley et al. Ophthal. Physiol. Opt., vol. 11, Jan. 1991, pp. 91-93.

Subjective Depth-of-Focus of the Eye. Atchison et al. Optometry and Vision Science, vol. 74, No. 7, Jul. 1997, pp. 511-520.

Subjective Sensitivity to Small Changes in the Contrast of a Suprathreshold Grating, The. Walsh et al. Vision Res., vol. 30, No. 1, pp. 163-193, 1990.

Surface Modification Properties of Parylene for Medical Applications, The. Wolgemuth, Lonny.Business Briefing: Medical Device Manfacturing & Technology 2002, pp. 1-4.

Surface tension control of collagen biomaterials by the selective hydrolysis of internal carboxyamides of the protein matrix. Revista Brasileira de Engenharia Biomedica, v. 15, n. 1-2, p. 55-61, Jan./ago 1999.

Surgeon: Severe corneal lesions after LASIK are not stage 4 DLK. Piechocki, Michael. Ocular SurgeryNews; Jan. 1, 2003, pp. 16-17.

Takahashi, E. "Use and Interpretation of the Pinhole Test" The Optometric Weekly, pp. 83-86 1965.

Theoretical and practical performance of a concentric bifocal intraocular implant lens. Charman, W.N. Vision Research 38 (1998) 2841-2853.

Use of a digital infrared pupillometer to assess patient suitability for refractive surgery. Rosen et al. J Cataract Refract Surg., vol. 28: Aug. 2002. pp. 1433-1438.

Vision and driving—a literature review and commentary. Charman, W.N. Ophthal. Physiol. Opt., vol. 17, No. 5, pp. 371-391, 1997.

Wesley, N. K. "Research on the Multi-Range Lens," pp. 18-24, 1970.

Zavala et al., "Refractive Keratoplosty: Lathing and Cyropreservation," CLAO Journal, Apr. 1985, 11:155-162.

Brooks, J. et al., Identification of a vimentin-reactive Peptide associated with ocular lens membranes as cytokeratin, Ophthalmic Res., Jan.-Feb. 2003, pp. 8-11, vol. 35.

Chow, C., et al., Broadband optical ultrasound sensor with a unique open-cavity structure, J. Biomed. Opt., Jan. 2011, pp. 017001-1-017001-6, vol. 16.

FDA Summary of Safety and Effectiveness Data for Tecnis Multifocal Posterior Chamber Intraocular Lens, Models ZM900 and ZMA00, 2009.

FDA Summary of Safety and Effectiveness Data for The Advanced Vision Science, Inc. XACT Foldable Hydrophopic Acrylic Ultraviolet Light-Absorbing Posterior Chamber Intraocular Lens (Model X-60 and Model X-70), 2009.

FDA Summary of Safety and Effectiveness Data for EC-3 IOL, (Models EC-3 IOL and EC-3 Precision Aspheric Lens), 2010.

FDA Summary of Safety and Effectiveness Data for Aaren Scientific's EC-3 IOL, 2010.

FDA Summary of Safety and Effectiveness Data for XACT Foldable Hydrophopic Acrylic UV Absorbing Posterior Chamber Intraocular Lens discussing clinical investigation beginning on May 8, 2002.

Gamez, G., et al., Development of a pulsed radio frequency glow discharge for three-dimensional elemental surface imaging. 1. Application to biopolymer analysis, Anal. Chem., Feb. 2007, pp. 1317-1326, vol. 79.

Glasier, M., et al., A solid-phase assay for the quantitation of total protein eluted from balafilcon, lotrafilcon, and etafilcon contact lenses, Current Eye Research, 2008, pp. 631-640, vol. 33.

Hara, T., et al., Accommodative intraocular lens with spring action. Part 1. Design and placement in an excised animal eye, Ophthalmic Surg., Feb. 1990, pp. 128-133, vol. 21.

Hara, T., et al., Ten-year results of anterior chamber fixation of the posterior chamber intraocular lens, Arch. Ophthalmol., Aug. 2004, pp. 1112-1116.

Hayasaka, S., et al., Scanning electron microscopic study of polyvinylidene fluoride degradation by ocular tissue extracts, Jpn. J. Ophthalmol., 1984, pp. 131-135, vol. 28.

Hayashi, K., et al., Intraocular lens factors that may affect anterior capsule contraction, Ophthalmology, Feb. 2005, pp. 286-292, vol. 112.

Hayashi, K., et al., Comparison of decentration and tilt between one piece and three piece polymethyl methacrylate intraocular lenses, Br. J. Ophthalmol., Apr. 1998, pp. 419-422, vol. 82.

Hidaka, T., et al, Adaptive optics instrumentation in submillimeter/terahertz spectroscopy with a flexible polyvinylidene fluoride cladding hollow waveguide, Rev. Sci. Instrum., 2007, pp. 086109-1-086109-2, vol. 78.

International Search Report and Written Opinion in PCT Application No. PCT/US/2005/043108 dated Aug. 30, 2006 in 16 pages.

Izak, A., et al., Loop memory of haptic materials in posterior chamber intraocular lenses, J. Cataract Refract. Surg., Jul. 2002, pp. 1229-1235, vol. 28.

Kimura, W., et al., Comparison of shape recovery ratios in various IOL haptics, Nippon Ganka Gakkai Zasshi, Jun. 1991, pp. 548-555, vol. 95.

Kimura, W., et al., Comparison of shape recovery ratios in various intraocular lens haptics, J. Cataract. Refract. Surg., Nov. 1992, pp. 547-553, vol. 18.

Kimura, W., et al., Comparison of shape recovery ratios of single-piece poly(methyl methacrylate) intraocular lens haptics., J. Cataract. Refract. Surg., Sep. 1993, pp. 635-639, vol. 19.

Ko, A., et al., Seroreactivity against aqueous-soluble and detergent-soluble retinal proteins in posterior uveitis, Arch. Ophthalmol., Apr. 2011, pp. 415-420, vol. 129.

Kocak, N., et al., Intraocular lens haptic fracturing with the neodymium:YAG laser in vitro study, J. Cataract Refract. Surg., Apr. 2006, pp. 662-665, vol. 32.

Moran, C., et al. Polyvinylidene flouride polymer applied in an intraocular pressure sensor, Jpn. J. Appl. Phys., 2005, pp. L885-L887, vol. 44, Issue 27.

Prince, S., et al., Sorption of alkylbenzyldimethylammonium chloride homologs to various filter media used in processing ophthalmics, APhA Annual Meeting, 1996, pp. 103, vol. 143.

Shingleton, B., Reply: pupil stretch technique, J. Cataract Refract. Surg., 2007, pp. 362, vol. 33.

Subrayan, V., et al., Improving quality of vision with an anterior surface modified prolate intraocular lens: A prospective clinical trial, Int. J. Ophthalmol., Jun. 2008, pp. 122-124, vol. 1, No. 2.

Tasaki, I., et al., Demonstration of heat production associated with spreading depression in the amphibian retina, Biochem. Biophys. Res. Commun., Jan. 1991, pp. 293-297, vol. 174.

* cited by examiner

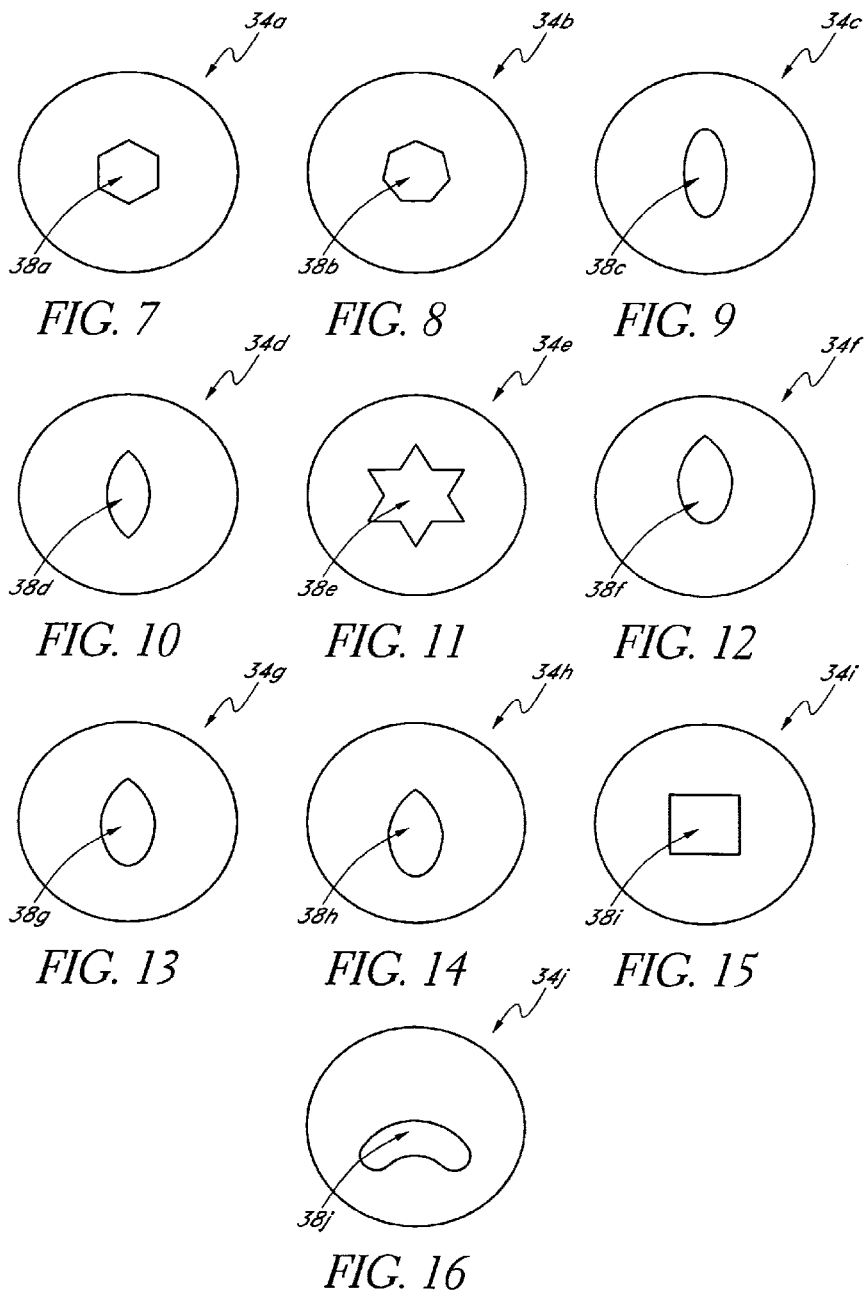

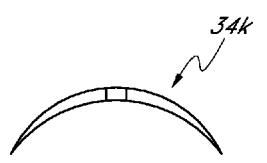
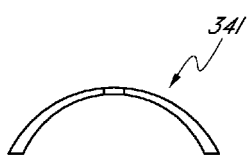
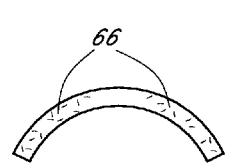
FIG. 17  FIG. 18  FIG. 19
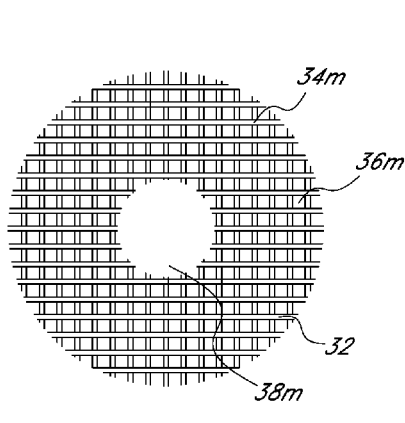
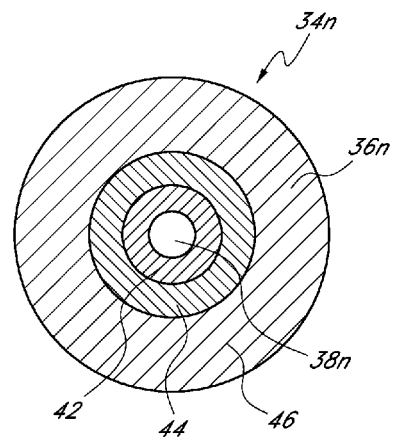
FIG. 20  FIG. 22
FIG. 21  FIG. 23

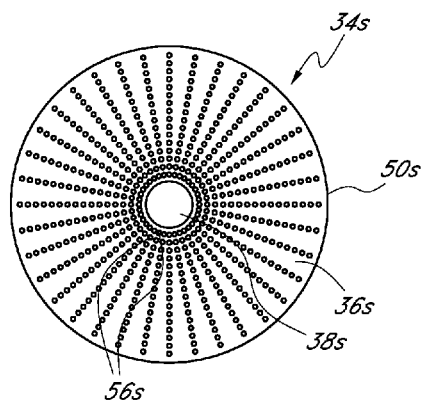
FIG. 32
FIG. 33
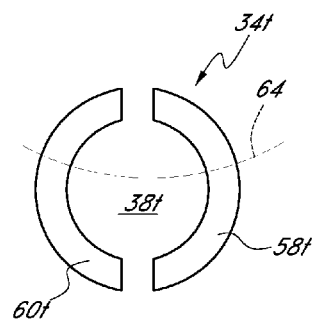
FIG. 34
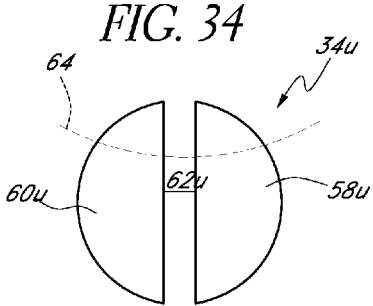
FIG. 35
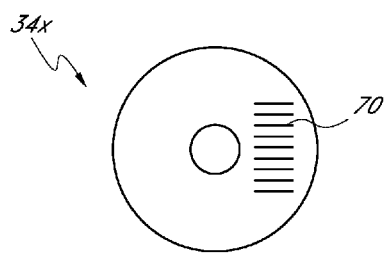
FIG. 39
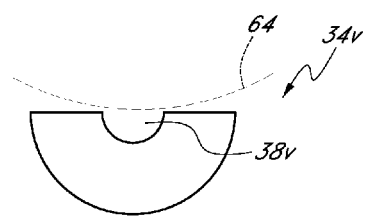
FIG. 36
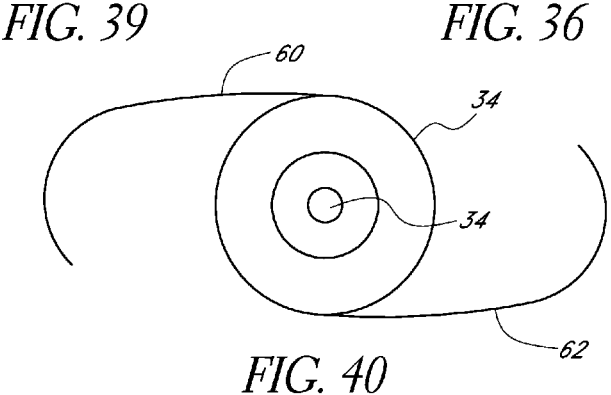
FIG. 40

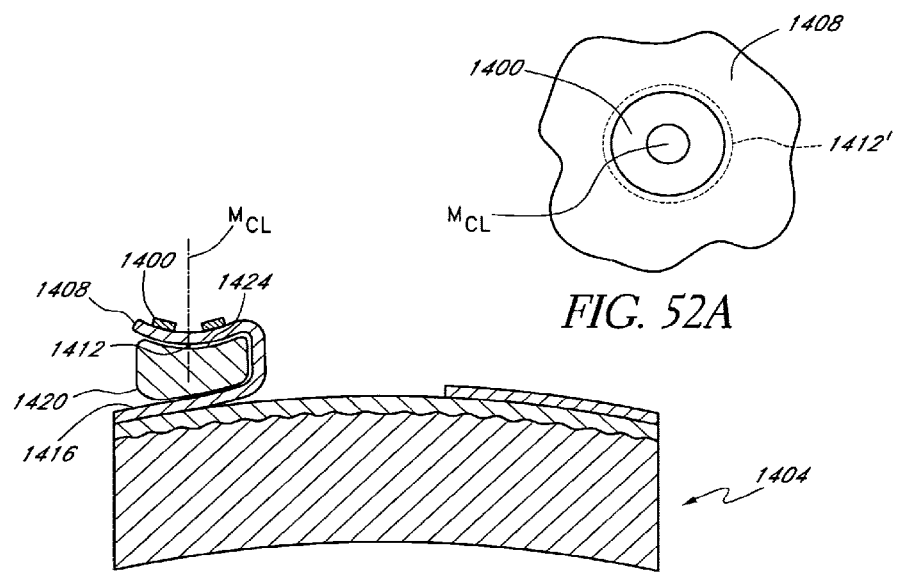
FIG. 52A
FIG. 52
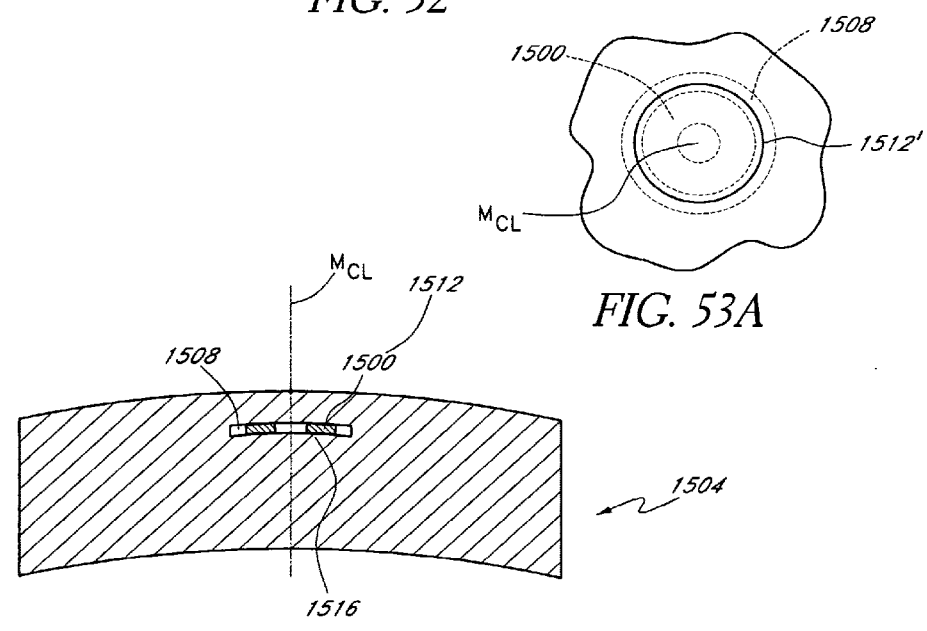
FIG. 53A
FIG. 53

OPHTHALMIC DEVICES HAVING A DEGRADATION RESISTANT POLYMER

RELATED APPLICATIONS

This application is a continuation of U.S. patent application Ser. No. 11/106,043, filed Apr. 14, 2005 and issued as U.S. Pat. No. 7,976,577, the entirety of which is hereby incorporated by reference.

BACKGROUND OF THE INVENTION

1. Field of the Invention

This application is related to ophthalmic devices. More particularly, this application is directed to ophthalmic devices that are configured not to degrade over the useful life of the ophthalmic device.

2. Description of the Related Art

A normally functioning human eye is capable of selectively focusing on either near or far objects through a process known as accommodation. Accommodation is achieved by inducing deformation in a lens located inside the eye, which is normally referred to as the "intraocular lens". Such deformation is induced by muscles called ciliary muscles. As some individuals age, the ability to accommodate diminishes and these individuals cannot see up close without vision correction. If far vision also is deficient, such individuals are prescribed bifocal lenses.

While this approach is sometimes satisfactory, some have proposed implanting devices inside the eye to improve accommodation for older patients. One such implant is a pin-hole imaging device that can be implanted in the cornea of an eye. While this type of device has been discussed in various contexts, and a need for the device has been identified, no such device is currently on the market.

Several factors make a successful device of this type elusive. In particular, the device needs to improve the depth of field of a patient's vision and, because it is surgically implanted, the device has to have a very long life-span. No known device has been proposed that has an adequate life-span.

Because corneal implants are exposed to a great deal of sunlight during their lifetime, resistance to degradation of the polymer due to UV exposure is important. In the contact lens and IOL arts, commercially available stabilizers have been added to the lenses to prevent degradation of the lenses due to this exposure and also to exposure to UV light used as a means of sterilization. Stabilizers dissipate the energy of ultraviolet rays to prevent degradation of the lens material. The stabilizers may be physically combined with the polymer or they may be part of a monomer which is copolymerizable with the polymeric material which forms the lens. Copolymerization reduces extractability, a problem with many stabilizers that are merely physically combined with a polymer.

SUMMARY OF THE INVENTION

Notwithstanding the foregoing, there remains a need for a corneal inlay device that is sufficiently resistant to degradation of the type described above and for this and other similar applications.

In accordance with one embodiment, there is provided a mask optic configured to be implanted in a cornea of a patient. The mask optic comprises a body formed from, including, or coated with a material comprising a halogenated polymeric material, preferably a fluorinated or highly fluorinated polymeric material, the body having a light transmitting portion, a light blocking portion disposed about the light transmitting portion, an outer periphery surrounding the light blocking portion, an anterior surface, and a posterior surface, the anterior surface configured to reside adjacent a first intracorneal layer, the posterior surface configured to reside adjacent a second intracorneal layer, wherein the body has a substantially constant thickness between the anterior and posterior surfaces, wherein the number of carbon-fluorine bonds in the highly fluorinated polymeric material equals or exceeds the number of carbon-hydrogen bonds.

In a preferred embodiment, the material forming the light blocking portion of the body comprises an opacification agent.

In accordance with another embodiment, there is provided a mask optic comprising an aperture having a major axis of about 2.2 mm or less, and an annular body extending between the aperture and an outer periphery of the mask, the annular body having an anterior surface and a posterior surface, the annular body being formed of a material comprising a highly fluorinated polymeric material and an opacification agent, the opacification agent being present in sufficient quantity to prevent at least a substantial portion of light incident on the anterior surface from being transmitted from the anterior surface to the posterior surface.

The opacification agent is preferably selected from the group consisting of organic dyes and/or pigments, and inorganic dyes and/or pigments. In certain preferred embodiments, the highly fluorinated polymeric material comprises polyvinylidene fluoride (PVDF) or is made from the polymerization of monomer substantially comprising vinylidene fluoride and/or the opacification agent is carbon.

BRIEF DESCRIPTION OF THE DRAWINGS

FIG. 7 is a frontal plan view of an embodiment of a mask with a hexagon-shaped pinhole like aperture.

FIG. 8 is a frontal plan view of an embodiment of a mask with an octagon-shaped pinhole like aperture.

FIG. 9 is a frontal plan view of an embodiment of a mask with an oval-shaped pinhole like aperture.

FIG. 10 is a frontal plan view of an embodiment of a mask with a pointed oval-shaped pinhole like aperture.

FIG. 11 is a frontal plan view of an embodiment of a mask with a star-shaped pinhole like aperture.

FIG. 12 is a frontal plan view of an embodiment of a mask with a teardrop-shaped pinhole like aperture spaced above the true center of the mask.

FIG. 13 is a frontal plan view of an embodiment of a mask with a teardrop-shaped pinhole like aperture centered within the mask.

FIG. 14 is a frontal plan view of an embodiment of a mask with a teardrop-shaped pinhole like aperture spaced below the true center of the mask.

FIG. 15 is a frontal plan view of an embodiment of a mask with a square-shaped pinhole like aperture.

FIG. 16 is a frontal plan view of an embodiment of a mask with a kidney-shaped oval pinhole like aperture.

FIG. 17 is a side view of an embodiment of a mask having varying thickness.

FIG. 18 is a side view of another embodiment of a mask having varying thickness.

FIG. 19 is a side view of an embodiment of a mask with a gel to provide opacity to the lens.

FIG. 20 is a frontal plan view of an embodiment of a mask with a weave of polymeric fibers.

FIG. 21 is a side view of the mask of FIG. 20.

FIG. 22 is a frontal plan view of an embodiment of a mask having regions of varying opacity.

FIG. 23 is a side view of the mask of FIG. 22.

FIG. 32 is a frontal plan view of an embodiment of a mask that includes a central pinhole like aperture and a plurality of holes radially spaced from the aperture.

FIG. 33 is a side view of the mask of FIG. 32.

FIG. 34 is an embodiment of a mask that includes two semi-circular mask portions.

FIG. 35 is an embodiment of a mask including two half-moon shaped portions.

FIG. 36 is an embodiment of a mask that includes a half-moon shaped region and a centrally-located pinhole like aperture.

FIG. 39 is an embodiment of a mask that includes a barcode formed on the annular region of the mask.

FIG. 40 is another embodiment of a mask that includes connectors for securing the mask within the eye.

FIG. 52 is a cross-sectional view of an eye illustrating a treatment of a patient wherein a flap is opened to place an implant and a location is marked for placement of the implant.

FIG. 52A is a partial plan view of the eye of FIG. 52 wherein an implant has been applied to a corneal flap and positioned with respect to a ring.

FIG. 53 is a cross-sectional view of an eye illustrating a treatment of a patient wherein a pocket is created to place an implant and a location is marked for placement of the implant.

FIG. 53A is a partial plan view of the eye of FIG. 53 wherein an implant has been positioned in a pocket and positioned with respect to a ring.

DETAILED DESCRIPTION OF THE PREFERRED EMBODIMENT

This application is directed to masks for improving the depth of focus of an eye of a patient and methods and apparatuses for making such masks. The masks generally employ pin-hole vision correction and have nutrient transport structures in some embodiments. The masks may be applied to the eye in any manner and in any location, e.g., as an implant in the cornea (sometimes referred to as a "corneal inlay"). The masks can also be embodied in or combined with lenses and applied in other regions of the eye, e.g., as or in combination with contact lenses or intraocular lenses. In some applications, discussed further below, the masks are formed of a stable material, e.g., one that can be implanted permanently.

I. Overview of Pin-Hole Vision Correction

As discussed above, mask that has a pinhole aperture may be used to improve the depth of focus of a human eye. As discussed above, presbyopia is a problem of the human eye that commonly occurs in older human adults wherein the ability to focus becomes limited to inadequate range. FIGS.

1-6 illustrate how presbyopia interferes with the normal function of the eye and how a mask with a pinhole aperture mitigates the problem.

Figure 1:
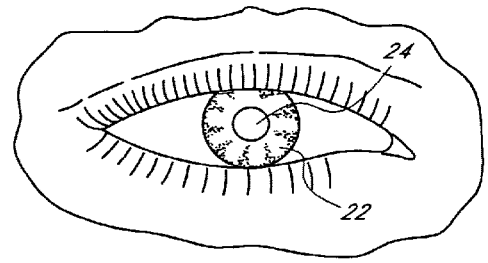
FIG. 1 is a plan view of the human eye.
Figure 2:
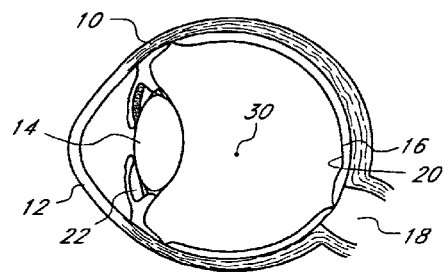
FIG. 2 is a cross-sectional side view of the human eye.

FIG. 1 shows the human eye, and FIG. 2 is a side view of the eye 10. The eye 10 includes a cornea 12 and an intraocular lens 14 posterior to the cornea 12. The cornea 12 is a first focusing element of the eye 10. The intraocular lens 14 is a second focusing element of the eye 10. The eye 10 also includes a retina 16, which lines the interior of the rear surface of the eye 10. The retina 16 includes the receptor cells which are primarily responsible for the sense of vision. The retina 16 includes a highly sensitive region, known as the macula, where signals are received and transmitted to the visual centers of the brain via the optic nerve 18. The retina 16 also includes a point with particularly high sensitivity 20, known as the fovea. As discussed in more detail in connection with FIG. 8, the fovea 20 is slightly offset from the axis of symmetry of the eye 10.

The eye 10 also includes a ring of pigmented tissue known as the iris 22. The iris 22 includes smooth muscle for controlling and regulating the size of an opening 24 in the iris 22, which is known as the pupil. An entrance pupil 26 is seen as the image of the iris 22 viewed through the cornea 12 (See FIG. 4).

The eye 10 resides in an eye-socket in the skull and is able to rotate therein about a center of rotation 30.

Figure 3:
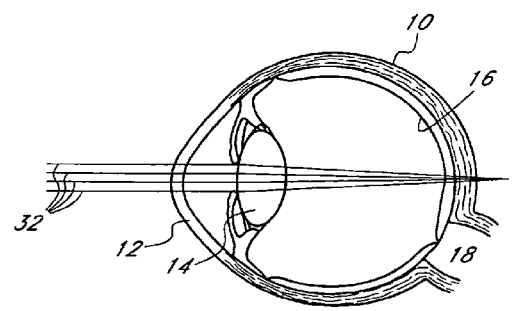
FIG. 3 is a cross-sectional side view of the human eye of a presbyopic patient wherein the light rays converge at a point behind the retina of the eye.

FIG. 3 shows the transmission of light through the eye 10 of a presbyotic patient. Due to either an aberration in the cornea 12 or the intraocular lens 14, or loss of muscle control, light rays 32 entering the eye 10 and passing through the cornea 12 and the intraocular lens 14 are refracted in such a way that the light rays 32 do not converge at a single focal point on the retina 16. FIG. 3 illustrates that in a presbyotic patient, the light rays 32 often converge at a point behind the retina 16. As a result, the patient experiences blurred vision.

Figure 4:
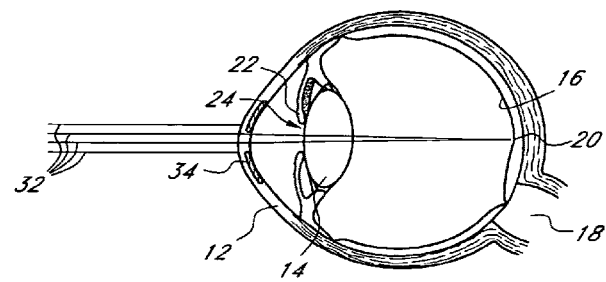
FIG. 4 is a cross-sectional side view of a presbyopic eye implanted with one embodiment of a mask wherein the light rays converge at a point on the retina.

Turning now to FIG. 4, there is shown the light transmission through the eye 10 to which a mask 34 has been applied. The mask 34 is shown implanted in the cornea 12 in FIG. 4. However, as discussed below, it will be understood that the mask 34 can be, in various modes of application, implanted in the cornea 12 (as shown), used as a contact lens placed over the cornea 12, incorporated in the intraocular lens 14 (including the patient's original lens or an implanted lens), or otherwise positioned on or in the eye 10. In the illustrated embodiment, the light rays 32 that pass through the mask 34, the cornea 12, and the lens 14 converge at a single focal point on the retina 16. The light rays 32 that would not converge at the single point on retina 16 are blocked by the mask 34. As discussed below, it is desirable to position the mask 34 on the eye 10 so that the light rays 32 that pass through the mask 34 converge at the fovea 20.

Figure 6:
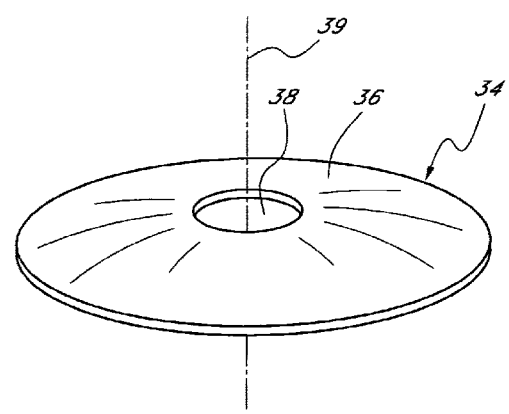
FIG. 6 is a perspective view of one embodiment of a mask.

Turning now to FIG. 6, there is shown one embodiment of the mask 34. A variety of variations of the mask 34 are discussed hereinbelow. Section III discusses some materials that can be used to make the mask 34 and any of the variation thereof discussed hereinbelow. As seen, the mask 34 preferably includes an annular region 36 surrounding a pinhole opening or aperture 38 substantially centrally located on the mask 34. The pinhole aperture 38 is generally located around a central axis 39, referred to herein as the optical axis of the mask 34. The pinhole aperture 38 preferably is in the shape of a circle. It has been reported that a circular aperture, such as the aperture 38 may, in some patients, produce a so-called "halo effect" where the patient perceives a shimmering image around the object being viewed. Accordingly, it may be desirable to provide an aperture 38 in a shape that diminishes, reduces, or completely eliminates the so-called "halo effect."

II. Masks Employing Pin-Hole Correction

FIGS. 7-42 illustrate a variety of embodiments of masks that can improve the vision of a patient with presbyopia. The masks described in connection with FIG. 7-42 are similar to the mask 34, except as described differently below. Any of the masks discussed below, e.g., those shown in FIGS. 7-42, can be made of the materials discussed below in Section III. The mask 34 and any of the masks discussed below can include a locator structure, such as is discussed in an application filed Apr. 14, 2005 with the title "OCULAR INLAY WITH LOCATOR", which is incorporated herein by reference in its entirety. The masks described in connection with FIGS. 7-42 can be used and applied to the eye 10 of a patient in a similar fashion to the mask 34. For example, FIG. 7 shows an embodiment of a mask 34a that includes an aperture 38a formed in the shape of a hexagon. FIG. 8 shows another embodiment of a mask 34b that includes an aperture 38b formed in the shape of an octagon. FIG. 9 shows another embodiment of a mask 34c that includes an aperture 38c formed in the shape of an oval, while FIG. 10 shows another embodiment of a mask 34d that includes an aperture 38d formed in the shape of a pointed oval. FIG. 11 shows another embodiment of a mask 34e wherein the aperture 38e is formed in the shape of a star or starburst.

FIGS. 12-14 illustrate further embodiments that have tear-drop shaped apertures. FIG. 12 shows a mask 34f that has a tear-drop shaped aperture 38f that is located above the true center of the mask 34f FIG. 13 shows a mask 34g that has a tear-drop shaped aperture 38g that is substantially centered in the mask 34g. FIG. 14 shows a mask 34h that has a tear-drop shaped aperture 38h that is below the true center of the mask 34h. FIG. 12-14 illustrate that the position of aperture can be tailored, e.g., centered or off-center, to provide different effects. For example, an aperture that is located below the true center of a mask generally will allow more light to enter the eye because the upper portion of the aperture 34 will not be covered by the eyelid of the patient. Conversely, where the aperture is located above the true center of the mask, the aperture may be partially covered by the eyelid. Thus, the above-center aperture may permit less light to enter the eye.

FIG. 15 shows an embodiment of a mask 34i that includes an aperture 38i formed in the shape of a square. FIG. 16 shows an embodiment of a mask 34j that has a kidney-shaped aperture 38j. It will be appreciated that the apertures shown in FIGS. 7-16 are merely exemplary of non-circular apertures. Other shapes and arrangements may also be provided and are within the scope of the present invention.

The mask 34 preferably has a constant thickness, as discussed below. However, in some embodiments, the thickness of the mask may vary between the inner periphery (near the aperture 38) and the outer periphery. FIG. 17 shows a mask 34k that has a convex profile, i.e., that has a gradually decreasing thickness from the inner periphery to the outer periphery. FIG. 18 shows a mask 34l that has a concave profile, i.e., that has a gradually increasing thickness from the inner periphery to the outer periphery. Other cross-sectional profiles are also possible.

Figure 5:
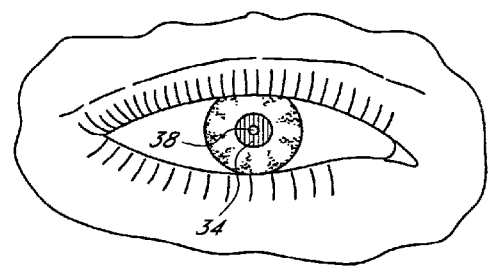
FIG. 5 is a plan view of the human eye with a mask applied thereto.

The annular region 36 is at least partially and preferably completely opaque. The opacity of the annular region 36 prevents light from being transmitted through the mask 34 (as generally shown in FIG. 5). Opacity of the annular region 36 may be achieved in any of several different ways.

For example, in one embodiment, the material used to make mask 34 may be naturally opaque. Alternatively, the material used to make the mask 34 may be substantially clear, but treated with a dye or other pigmentation agent to render region 36 substantially or completely opaque. In still another example, the surface of the mask 34 may be treated physically or chemically (such as by etching) to alter the refractive and transmissive properties of the mask 34 and make it less transmissive to light.

In still another alternative, the surface of the mask 34 may be treated with a particulate deposited thereon. For example, the surface of the mask 34 may be deposited with particulate of titanium, gold or carbon to provide opacity to the surface of the mask 34. In another alternative, the particulate may be encapsulated within the interior of the mask 34, as generally shown in FIG. 19. Finally, the mask 34 may be patterned to provide areas of varying light transmissivity, as generally shown in FIGS. 24-33, which are discussed in detail below.

Turning to FIG. 20, there is shown a mask 34m formed or made of a woven fabric, such as a mesh of polyester fibers. The mesh may be a cross-hatched mesh of fibers. The mask 34m includes an annular region 36m surrounding an aperture 38m. The annular region 36m comprises a plurality of generally regularly positioned apertures 36m in the woven fabric allow some light to pass through the mask 34m. The amount of light transmitted can be varied and controlled by, for example, moving the fibers closer together or farther apart, as desired. Fibers more densely distributed allow less light to pass through the annular region 36m. Alternatively, the thickness of fibers can be varied to allow more or less light through the openings of the mesh. Making the fiber strands larger results in the openings being smaller.

FIG. 22 shows an embodiment of a mask 34n that includes an annular region 36n that has sub-regions with different opacities. The opacity of the annular region 36n may gradually and progressively increase or decrease, as desired. FIG. 22 shows one embodiment where a first area 42 closest to an aperture 38n has an opacity of approximately 43%. In this embodiment, a second area 44, which is outlying with respect to the first area 42, has a greater opacity, such as 70%. In this embodiment, a third area 46, which is outlying with respect to the second area 42, has an opacity of between 85 to 100%. The graduated opacity of the type described above and shown in FIG. 22 is achieved in one embodiment by, for example, providing different degrees of pigmentation to the areas 42, 44 and 46 of the mask 34n. In another embodiment, light blocking materials of the type described above in variable degrees may be selectively deposited on the surface of a mask to achieve a graduated opacity.

In another embodiment, the mask may be formed from co-extruded rods made of material having different light transmissive properties. The co-extruded rod may then be sliced to provide disks for a plurality of masks, such as those described herein.

Figure 24:
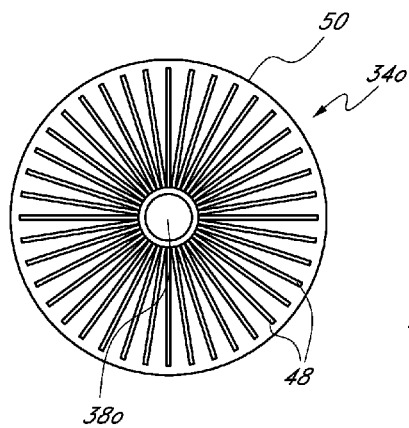
FIG. 24 is a frontal plan view of an embodiment of a mask that includes a centrally located pinhole like aperture and radially extending slots emanating from the center to the periphery of the mask.

FIGS. 24-33 shows examples of masks that have been modified to provide regions of differing opacity. For example, FIG. 24 shows a mask 34o that includes an aperture 38o and a plurality of cutouts 48 in the pattern of radial spokes extending from near the aperture 38o to an outer periphery 50 of the mask 34o. FIG. 24 shows that the cutouts 48 are much more densely distributed about a circumference of the mask near aperture 38o than are the cutouts 48 about a circumference of the mask near the outer periphery 50. Accordingly, more light passes through the mask 34o nearer aperture 38o than near the periphery 50. The change in light transmission through the mask 34o is gradual.

Figure 26:
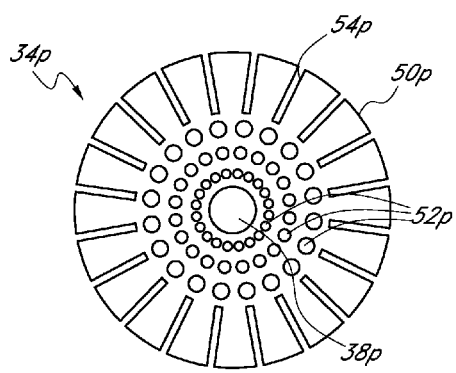
FIG. 26 is a frontal plan view of an embodiment of a mask that includes a central pinhole like aperture, surrounded by a plurality of holes radially spaced from the pinhole like aperture and slots extending radially spaced from the holes and extending to the periphery of the mask.
Figure 27:
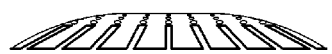
FIG. 27 is a side view of the mask of FIG. 26.

FIGS. 26-27 show another embodiment of a mask 34p. The mask 34p includes an aperture 38p and a plurality of circular cutouts 49p, and a plurality of cutouts 51p. The circular cutouts 49p are located proximate the aperture 38p. The cutouts 51p are located between the circular cutouts 49p and the periphery 50p. The density of the circular cutouts 49p generally decreases from the near the aperture 38p toward the periphery 50p. The periphery 50p of the mask 34p is scalloped by the presence of the cutouts 54p, which extend inward from the periphery 50p, to allow some light to pass through the mask at the periphery 50p.

Figure 28:
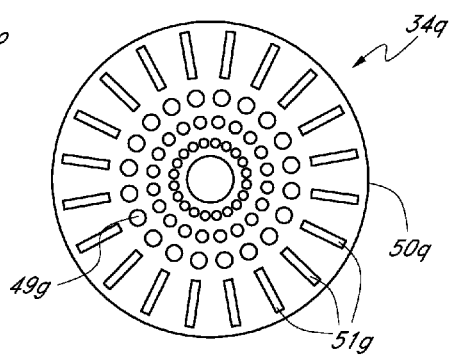
FIG. 28 is a frontal plan view of an embodiment of a mask that includes a central pinhole like aperture, a region that includes a plurality of holes radially spaced from the aperture, and a region that includes rectangular slots spaced radially from the holes.
Figure 25:
FIG. 25 is a side view of the mask of FIG. 24.
Figure 29:
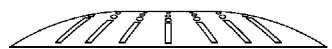
FIG. 29 is a side view of the mask of FIG. 28.

FIGS. 28-29 shows another embodiment similar to that of FIGS. 26-27 wherein a mask 34q includes a plurality of circular cutouts 49q and a plurality of cutouts 51q. The cutouts 51q are disposed along the outside periphery 50q of the mask 34q, but not so as to provide a scalloped periphery.

Figure 30:
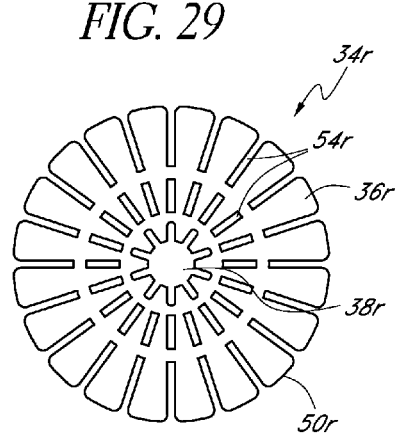
FIG. 30 is a frontal plan view of an embodiment of a mask that includes a non-circular pinhole like aperture, a first set of slots radially spaced from the aperture, and a region that includes a second set of slots extending to the periphery of the mask and radially spaced from the first set of slots.
Figure 31:
FIG. 31 is a side view of the mask of FIG. 30.

FIGS. 30 and 31 illustrate an embodiment of a mask 34r that includes an annular region 36r that is patterned and an aperture 38r that is non-circular. As shown in FIG. 30, the aperture 38r is in the shape of a starburst. Surrounding the aperture 38r is a series of cutouts 51r that are more densely spaced toward the aperture 38r. The mask 34r includes an outer periphery 50r that is scalloped to provide additional light transmission at the outer periphery 50r.

FIGS. 32 and 33 show another embodiment of a mask 34s that includes an annular region 36s and an aperture 38s. The annular region 36s is located between an outer periphery 50s of the mask 34s and the aperture 38s. The annular region 36s is patterned. In particular, a plurality of circular openings 56s is distributed over the annular region 36s of the mask 34s. It will be appreciated that the density of the openings 56s is greater near the aperture 38s than near the periphery 50s of the mask 34s. As with the examples described above, this results in a gradual increase in the opacity of the mask 34s from aperture 38s to periphery 50s.

FIGS. 34-36 show further embodiments. In particular, FIG. 34 shows a mask 34t that includes a first mask portion 58t and a second mask portion 43t. The mask portions 58t, 43t are generally "C-shaped." As shown in FIG. 34, the mask portions 58t, 43t are implanted or inserted such that the mask portions 58t, 43t define a pinhole or aperture 38t.

FIG. 35 shows another embodiment wherein a mask 34u includes two mask portions 58u, 43u. Each mask portion 58u, 43u is in the shape of a half-moon and is configured to be implanted or inserted in such a way that the two halves define a central gap or opening 45u, which permits light to pass therethrough. Although opening 45u is not a circular pinhole, the mask portions 58u, 43u in combination with the eyelid (shown as dashed line 64) of the patient provide a comparable pinhole effect.

FIG. 36 shows another embodiment of a mask 34v that includes an aperture 38v and that is in the shape of a half-moon. As discussed in more detail below, the mask 34v may be implanted or inserted into a lower portion of the cornea 12 where, as described above, the combination of the mask 34v and the eyelid 64 provides the pinhole effect.

Other embodiments employ different ways of controlling the light transmissivity through a mask. For example, the mask may be a gel-filled disk, as shown in FIG. 19. The gel may be a hydrogel or collagen, or other suitable material that is biocompatible with the mask material and can be introduced into the interior of the mask. The gel within the mask may include particulate 53 suspended within the gel. Examples of suitable particulate are gold, titanium, and carbon particulate, which, as discussed above, may alternatively be deposited on the surface of the mask.

The material of the mask 34 may be any biocompatible polymeric material. Where a gel is used, the material is suitable for holding a gel. Examples of suitable materials for the mask 34 include the preferred polymethylmethacrylate or other suitable polymers, such as polycarbonates and the like.

Of course, as indicated above, for non-gel-filled materials, a preferred material may be a fibrous material, such as a Dacron mesh.

The mask 34 may also be made to include a medicinal fluid, such as an antibiotic that can be selectively released after application, insertion, or implantation of the mask 34 into the eye of the patient. Release of an antibiotic after application, insertion, or implantation provides faster healing of the incision. The mask 34 may also be coated with other desired drugs or antibiotics. For example, it is known that cholesterol deposits can build up on the eye. Accordingly, the mask 34 may be provided with a releasable cholesterol deterring drug. The drug may be coated on the surface of the mask 34 or, in an alternative embodiment, incorporated into the polymeric material (such as PMMA) from which the mask 34 is formed.

Figure 37:
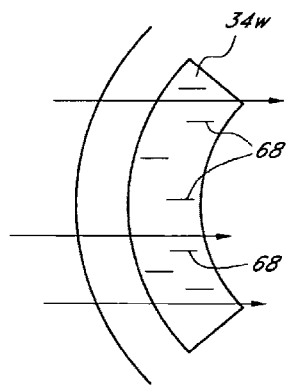
FIG. 37 is an enlarged, diagrammatic view of an embodiment of a mask that includes particulate structure adapted for selectively controlling light transmission through the mask in a low light environment.
Figure 38:
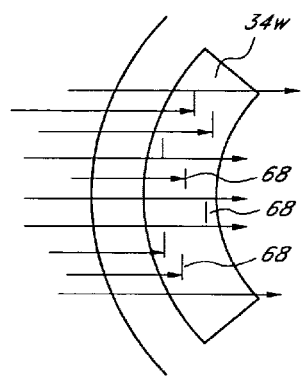
FIG. 38 is a view of the mask of FIG. 37 in a bright light environment.

FIGS. 37 and 38 illustrate one embodiment where a mask 34w comprises a plurality of nanites 68. "Nanites" are small particulate structures that have been adapted to selectively transmit or block light entering the eye of the patient. The particles may be of a very small size typical of the particles used in nanotechnology applications. The nanites 68 are suspended in the gel or otherwise inserted into the interior of the mask 34w, as generally shown in FIGS. 37 and 38. The nanites 68 can be preprogrammed to respond to different light environments.

Thus, as shown in FIG. 38, in a high light environment, the nanites 68 turn and position themselves to substantially and selectively block some of the light from entering the eye. However, in a low light environment where it is desirable for more light to enter the eye, nanites may respond by turning or be otherwise positioned to allow more light to enter the eye, as shown in FIG. 37.

Nano-devices or nanites are crystalline structures grown in laboratories. The nanites may be treated such that they are receptive to different stimuli such as light. In accordance with one aspect of the present invention, the nanites can be imparted with energy where, in response to a low light and high light environments, they rotate in the manner described above and generally shown in FIG. 38.

Nanoscale devices and systems and their fabrication are described in Smith et al., "Nanofabrication," Physics Today, February 1990, pp. 24-30 and in Craighead, "Nanoelectromechanical Systems," Science, Nov. 24, 2000, Vol. 290, pp. 1502-1505, both of which are incorporated by reference herein in their entirety. Tailoring the properties of small-sized particles for optical applications is disclosed in Chen et al. "Diffractive Phase Elements Based on Two-Dimensional Artificial Dielectrics," Optics Letters, Jan. 15, 1995, Vol. 20, No. 2, pp. 121-123, also incorporated by reference herein in its entirety.

Masks 34 made in accordance with the present invention may be further modified to include other properties. FIG. 39 shows one embodiment of a mask 34x that includes a bar code 70 or other printed indicia.

The masks described herein may be incorporated into the eye of a patient in different ways. For example, as discussed in more detail below in connection with FIG. 49, the mask 34 may be provided as a contact lens placed on the surface of the eyeball 10. Alternatively, the mask 34 may be incorporated in an artificial intraocular lens designed to replace the original lens 14 of the patient. Preferably, however, the mask 34 is provided as a corneal implant or inlay, where it is physically inserted between the layers of the cornea 12.

When used as a corneal implant, layers of the cornea 12 are peeled away to allow insertion of the mask 34. Typically, the optical surgeon (using a laser) cuts away and peels away a flap of the overlying corneal epithelium. The mask 34 is then inserted and the flap is placed back in its original position where, over time, it grows back and seals the eyeball. In some embodiments, the mask 34 is attached or fixed to the eye 10 by support strands 60 and 62 shown in FIG. 40 and generally described in U.S. Pat. No. 4,976,732, incorporated by reference herein in its entirety.

In certain circumstances, to accommodate the mask 34, the surgeon may be required to remove additional corneal tissue. Thus, in one embodiment, the surgeon may use a laser to peel away additional layers of the cornea 12 to provide a pocket that will accommodate the mask 34. Application of the mask 34 to the cornea 12 of the eye 10 of a patient is described in greater detail in connection with FIGS. 50A-51C.

Removal of the mask 34 may be achieved by simply making an additional incision in the cornea 12, lifting the flap and removing the mask 34. Alternatively, ablation techniques may be used to completely remove the mask 34.

Figure 41:
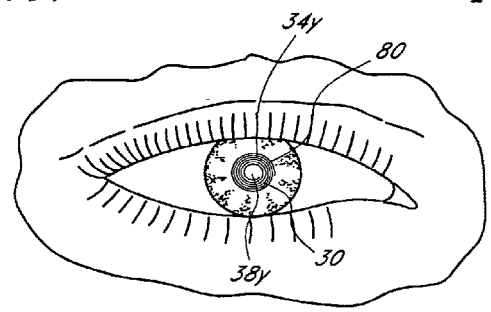
FIG. 41 is a plan view of an embodiment of a mask made of a spiraled fibrous strand.
Figure 42:
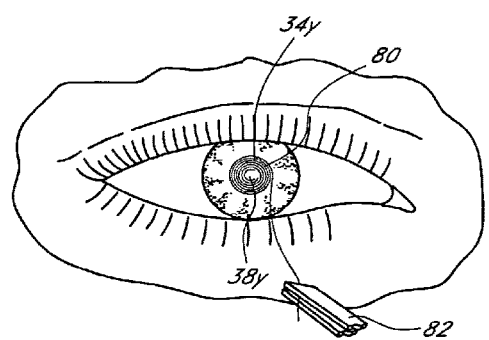
FIG. 42 is a plan view of the mask of FIG. 41 being removed from the eye.

FIGS. 41 and 42 illustrate another embodiment, of a mask 34y that includes a coiled strand 80 of a fibrous or other material. Strand 80 is coiled over itself to form the mask 34y, which may therefore be described as a spiral-like mask. This arrangement provides a pinhole or aperture 38y substantially in the center of the mask 34y. The mask 34y can be removed by a technician or surgeon who grasps the strand 80 with tweezers 82 through an opening made in a flap of the corneal 12. FIG. 42 shows this removal technique.

Further mask details are disclosed in U.S. Pat. No. 4,976,732, issued Dec. 11, 1990 and in U.S. Provisional Application Serial No. 43/473,824, filed May 28, 2003, both of which are incorporated by reference herein in their entirety.

III. Preferred UV-Resistant Polymeric Mask Materials

Because the mask has a very high surface to volume ratio and is exposed to a great deal of sunlight following implantation, the mask preferably comprises a material which has good resistance to degradation, including from exposure to ultraviolet (UV) or other wavelengths of light. Polymers including a UV absorbing component, including those comprising UV absorbing additives or made with UV absorbing monomers (including co-monomers), may be used in forming masks as disclosed herein which are resistant to degradation by UV radiation. Examples of such polymers include, but are not limited to, those described in U.S. Pat. Nos. 4,985,559 and 4,528,311, the disclosures of which are hereby incorporated by reference in their entireties. In a preferred embodiment, the mask comprises a material which itself is resistant to degradation by UV radiation. In one embodiment, the mask comprises a polymeric material which is substantially reflective of or transparent to UV radiation.

Alternatively, the mask may include a component which imparts a degradation resistive effect, or may be provided with a coating, preferably at least on the anterior surface, which imparts degradation resistance. Such components may be included, for example, by blending one or more degradation resistant polymers with one or more other polymers. Such blends may also comprise additives which provide desirable properties, such as UV absorbing materials. In one embodiment, blends preferably comprise a total of about 1-20 wt. %, including about 1-10 wt. %, 5-15 wt. %, and 10-20 wt. % of one or more degradation resistant polymers. In another embodiment, blends preferably comprise a total of about 80-100 wt. %, including about 80-90 wt. %, 85-95 wt. %, and 90-100 wt. % of one or more degradation resistant polymers. In another embodiment, the blend has more equivalent proportions of materials, comprising a total of about 40-60 wt. %, including about 50-60 wt. %, and 40-50 wt. % of one or more degradation resistant polymers. Masks may also include blends of different types of degradation resistant polymers, including those blends comprising one or more generally UV transparent or reflective polymers with one or more polymers incorporating UV absorption additives or monomers. These blends include those having a total of about 1-20 wt. %, including about 1-10 wt. %, 5-15 wt. %, and 10-20 wt. % of one or more generally UV transparent polymers, a total of about 80-100 wt. %, including about 80-90 wt. %, 85-95 wt. %, and 90-100 wt. % of one or more generally UV transparent polymers, and a total of about 40-60 wt. %, including about 50-60 wt. %, and 40-50 wt. % of one or more generally UV transparent polymers.

Preferred degradation resistant polymers include halogenated polymers. Preferred halogenated polymers include fluorinated polymers, that is, polymers having at least one carbon-fluorine bond, including highly fluorinated polymers. The term "highly fluorinated" as it is used herein, is a broad term used in its ordinary sense, and includes polymers having at least one carbon-fluorine bond (C—F bond) where the number of C—F bonds equals or exceeds the number of carbon-hydrogen bonds (C—H bonds). Highly fluorinated materials also include perfluorinated or fully fluorinated materials, materials which include other halogen substituents such as chlorine, and materials which include oxygen- or nitrogen-containing functional groups. For polymeric materials, the number of bonds may be counted by referring to the monomer(s) or repeating units which form the polymer, and in the case of a copolymer, by the relative amounts of each monomer (on a molar basis).

Preferred highly fluorinated polymers include, but are not limited to, polytetrafluoroethylene (PFTE or Teflon®), polyvinylidene fluoride (PVDF or Kynar®), poly- 1,1,2-trifluoroethylene, and perfluoroalkoxyethylene (PFA). Other highly fluorinated polymers include, but are not limited to, homopolymers and copolymers including one or more of the following monomer units: tetrafluoroethylene —(CF$_2$—CF$_2$)—; vinylidene fluoride —(CF$_2$—CH$_2$)—; 1,1,2-trifluoroethylene —(CF$_2$—CHF)—; hexafluoropropene —(CF(CF$_3$)-CF$_2$)—; vinyl fluoride —(CH$_2$—CHF)— (homopolymer is not "highly fluorinated"); oxygen-containing monomers such as —(O-CF$_2$)—, —(O—CF$_2$—CF$_2$)—, —(O—CF(CF$_3$)—CF$_2$)—; chlorine-containing monomers such as —(CF$_2$—CFCl)—. Other fluorinated polymers, such as fluorinated polyimide and fluorinated acrylates, having sufficient degrees of fluorination are also contemplated as highly fluorinated polymers for use in masks according to preferred embodiments. The homopolymers and copolymers described herein are available commercially and/or methods for their preparation from commercially available materials are widely published and known to those in the polymer arts.

Although highly fluorinated polymers are preferred, polymers having one or more carbon-fluorine bonds but not falling within the definition of "highly fluorinated" polymers as discussed above, may also be used. Such polymers include co-polymers formed from one or more of the monomers in the preceding paragraph with ethylene, vinyl fluoride or other monomer to form a polymeric material having a greater number of C—H bonds than C—F bonds. Other fluorinated polymers, such as fluorinated polyimide, may also be used. Other materials that could be used in some applications, alone or in combination with a fluorinated or a highly fluorinated polymer, are described in U.S. Pat. No. 4,985,559 and in U.S. Pat. No. 4,538,311, both of which are hereby incorporated by reference herein in their entirety.

The preceding definition of highly fluorinated is best illustrated by means of a few examples. One preferred UV-resistant polymeric material is polyvinylidene fluoride (PVDF), having a structure represented by the formula: —(CF$_2$—CH$_2$)$_n$—. Each repeating unit has two C—H bonds, and two C—F bonds. Because the number of C—F bonds equals or exceeds the number of C—H bonds, PVDF homopolymer is a "highly fluorinated" polymer. Another material is a tetrafluoroethylene/vinyl fluoride copolymer formed from these two monomers in a 2:1 molar ratio. Regardless of whether the copolymer formed is block, random or any other arrangement, from the 2:1 tetrafluoroethylene:vinyl fluoride composition one can presume a "repeating unit" comprising two tetrafluoroethylene units, each having four C—F bonds, and one vinyl fluoride unit having three C—H bonds and one C—F bond. The total bonds for two tetrafluoroethylenes and one vinyl fluoride are nine C—F bonds, and three C—H bonds. Because the number of C—F bonds equals or exceeds the number of C—H bonds, this copolymer is considered highly fluorinated.

Certain highly fluorinated polymers, such as PVDF, have one or more desirable characteristics, such as being relatively chemically inert and having a relatively high UV transparency as compared to their non-fluorinated or less highly fluorinated counterpart polymers. Although the applicant does not intend to be bound by theory, it is postulated that the electronegativity of fluorine may be responsible for many of the desirable properties of the materials having relatively large numbers of C—F bonds.

In preferred embodiments, at least a portion of the highly fluorinated polymer material forming the mask comprises an opacification agent which imparts a desired degree of opacity. In one embodiment, the opacification agent provides sufficient opacity to produce the depth of field improvements described herein, e.g., in combination with a transmissive aperture. In one embodiment, the opacification agent renders the material opaque. In another embodiment, the opacification agent prevents transmission of about 90 percent or more of incident light. In another embodiment, the opacification agent renders the material opaque. In another embodiment, the opacification agent prevents transmission of about 80 percent or more of incident light. Preferred opacification agents include, but are not limited to organic dyes and/or pigments, preferably black ones, such as azo dyes, hematoxylin black, and Sudan black; inorganic dyes and/or pigments, including metal oxides such as iron oxide black and ilminite, silicon carbide and carbon (e.g. carbon black, submicron powdered carbon). The foregoing materials may be used alone or in combination with one or more other materials. The opacification agent may be applied to one or more surfaces of the mask on all or some of the surface, or it may be mixed or combined with the polymeric material (e.g. blended during the polymer melt phase). Although any of the foregoing materials may be used, carbon has been found to be especially useful in that it does not fade over time as do many organic dyes, and that it also aids the UV stability of the material by absorbing UV radiation.

Some opacification agents, such pigments, which are added to blacken, darken or opacify portions of the mask may cause the mask to absorb incident radiation to a greater degree than mask material not including such agents. Because the matrix polymer that carries or includes the pigments may be subject to degradation from the absorbed radiation, it is preferred that the mask, which is thin and has a high surface area making it vulnerable to environmental degradation, be made of a material which is itself resistant to degradation such as from UV radiation, or that it be generally transparent to or non-absorbing of UV radiation. Use of a highly UV resistant and degradation resistant material, such as PVDF, which is highly transparent to UV radiation, allows for greater flexibility in choice of opacification agent because possible damage to the polymer caused by selection of a particular opacification agent is greatly reduced.

A number of variations of the foregoing embodiments of degradation resistant constructions are contemplated. In one variation, a mask is made almost exclusively of a material that is not subject to UV degradation. For example, the mask can be made of a metal, a highly fluorinated polymer, or another similar material. Construction of the mask with metal is discussed in more detail in U.S. application Ser. No. 11/000,562 filed Dec. 1, 2004 and entitled "Method of Making an Ocular Implant" and also in an application with the title "Method of Making an Ocular Implant" filed Apr. 14, 2005, both of which are incorporated herein in their entirety by reference. As used in this context, "exclusively" is a broad term that allows for the presence of some non-functional materials (e.g., impurities) and for an opacification agent, as discussed above. In other embodiments, the mask can include a combination of materials. For example, in one variation, the mask is formed primarily of any implantable material and is coated with a UV resistant material. In another variation, the mask includes one or more UV degradation inhibitors and/or one or more UV degradation resistant polymers in sufficient concentration such that the mask under normal use conditions will maintain sufficient functionality in terms of degradation to remain medically effective for at least about 5 years, preferably at least about 10 years, and in certain implementations at least about 20 years.

IV. Masks Configured to Reduce Visibile Diffraction Patterns

Many of the foregoing masks can be used to improve the depth of focus of a patient. Various additional mask embodiments are discussed below. Some of the embodiments described below include nutrient transport structures that are configured to enhance or maintain nutrient flow between adjacent tissues by facilitating transport of nutrients across the mask. The nutrient transport structures of some of the embodiments described below are configured to at least substantially prevent nutrient depletion in adjacent tissues. The nutrient transport structures can decrease negative effects due to the presence of the mask in adjacent corneal layers when the mask is implanted in the cornea, increasing the longevity of the masks. The inventors have discovered that certain arrangements of nutrient transport structures generate diffraction patterns that interfere with the vision improving effect of the masks described herein. Accordingly, certain masks are described herein that include nutrient transport structures that do not generate diffraction patterns or otherwise interfere with the vision enhancing effects of the mask embodiments.

Figure 43:
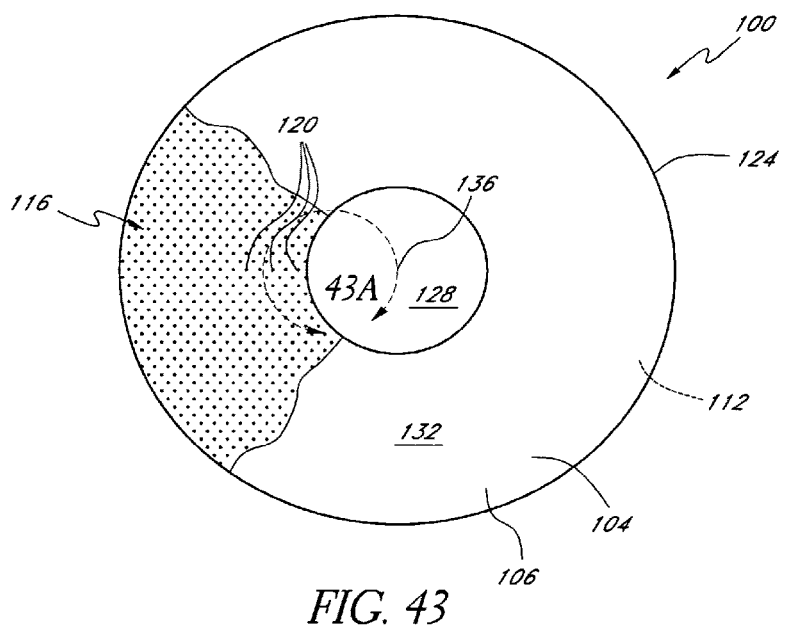
FIG. 43 is a top view of another embodiment of a mask configured to increase depth of focus.
Figure 43A:
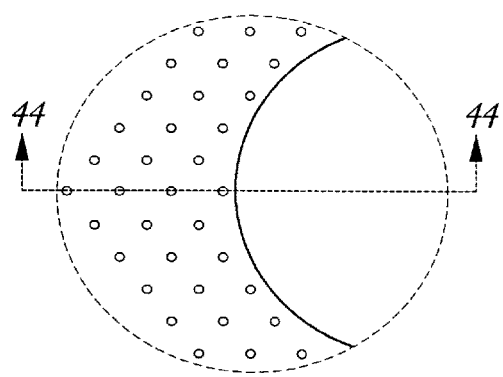
FIG. 43A is an enlarged view of a portion of the view of FIG. 43.
Figure 44A:
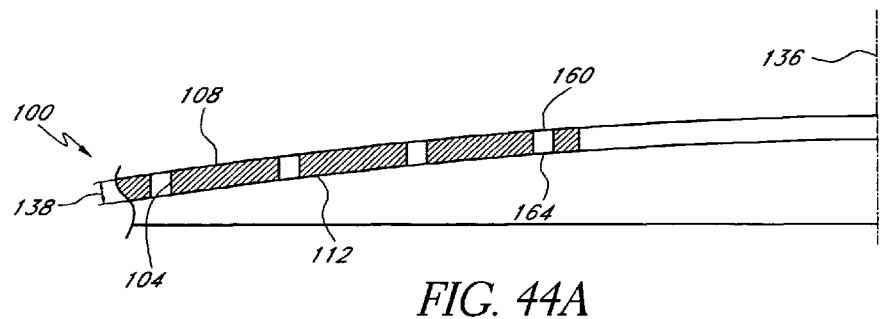
FIG. 44A is a cross-sectional view of the mask of FIG. 43A taken along the section plane 44-44.

FIGS. 43-44 show one embodiment of a mask 100 configured to increase depth of focus of an eye of a patient suffering from presbyopia. The mask 100 is similar to the masks hereinbefore described, except as described differently below. The mask 100 can be made of the materials discussed herein, including those discussed in Section III. Also, the mask 100 can be formed by any suitable process, such as those discussed below in connection with FIGS. 48a-48d with variations of such processes. The mask 100 is configured to be applied to an eye of a patient, e.g., by being implanted in the cornea of the patient. The mask 100 may be implanted within the cornea in any suitable manner, such as those discussed above in connection with FIGS. 50A-51C.

In one embodiment, the mask 100 includes a body 104 that has an anterior surface 108 and a posterior surface 112. In one embodiment, the body 104 is capable of substantially maintaining natural nutrient flow between the first corneal layer and the second corneal layer. In one embodiment, the material is selected to maintain at least about ninety-six percent of the natural flow of at least one nutrient (e.g., glucose) between a first corneal layer (e.g., the layer 1210) and a second corneal layer (e.g., the layer 1220). The body 104 may be formed of any suitable material, including at least one of an open cell foam material, an expanded solid material, and a substantially opaque material. In one embodiment, the material used to form the body 104 has relatively high water content.

In one embodiment, the mask 100 includes and a nutrient transport structure 116. The nutrient transport structure 116 may comprise a plurality of holes 120. The holes 120 are shown on only a portion of the mask 100, but the holes 120 preferably are located throughout the body 104 in one embodiment. In one embodiment, the holes 120 are arranged in a hex pattern, which is illustrated by a plurality of locations 120' in FIG. 45A. As discussed below, a plurality of locations may be defined and later used in the later formation of a plurality of holes 120 on the mask 100. The mask 100 has an outer periphery 124 that defines an outer edge of the body 104. In some embodiments, the mask 100 includes an aperture 128 at least partially surrounded by the outer periphery 124 and a non-transmissive portion 132 located between the outer periphery 124 and the aperture 128.

Preferably the mask 100 is symmetrical, e.g., symmetrical about a mask axis 136. In one embodiment, the outer periphery 124 of the mask 100 is circular. The masks in general have has a diameter within the range of from about 3 mm to about 8 mm, often within the range of from about 3.5 mm to about 6 mm, and less than about 6 mm in one embodiment. In another embodiment, the mask is circular and has a diameter in the range of 4 to 6 mm. In another embodiment, the mask 100 is circular and has a diameter of less than 4 mm. The outer periphery 124 has a diameter of about 3.8 mm in another embodiment. In some embodiments, masks that are asymmetrical or that are not symmetrical about a mask axis provide benefits, such as enabling a mask to be located or maintained in a selected position with respect to the anatomy of the eye.

The body 104 of the mask 100 may be configured to coupled with a particular anatomical region of the eye. The body 104 of the mask 100 may be configured to conform to the native anatomy of the region of the eye in which it is to be applied. For example, where the mask 100 is to be coupled with an ocular structure that has curvature, the body 104 may be provided with an amount of curvature along the mask axis 136 that corresponds to the anatomical curvature. For example, one environment in which the mask 100 may be deployed is within the cornea of the eye of a patient. The cornea has an amount of curvature that varies from person to person about a substantially constant mean value within an identifiable group, e.g., adults. When applying the mask 100 within the cornea, at least one of the anterior and posterior surfaces 108, 112 of the mask 100 may be provided with an amount of curvature corresponding to that of the layers of the cornea between which the mask 100 is applied.

In some embodiments, the mask 100 has a desired amount of optical power. Optical power may be provided by configuring the at least one of the anterior and posterior surfaces 108, 112 with curvature. In one embodiment, the anterior and posterior surfaces 108, 112 are provided with different amounts of curvature. In this embodiment, the mask 100 has varying thickness from the outer periphery 124 to the aperture 128.

In one embodiment, one of the anterior surface 108 and the posterior surface 112 of the body 104 is substantially planar. In one planar embodiment, very little or no uniform curvature can be measured across the planar surface. In another embodiment, both of the anterior and posterior surfaces 108, 112 are substantially planar. In general, the thickness of the inlay may be within the range of from about 1 micron to about 40 micron, and often in the range of from about 5 micron to about 20 micron. In one embodiment, the body 104 of the mask 100 has a thickness 138 of between about 5 micron and about 10 micron. In one embodiment, the thickness 138 of the mask 100 is about 5 micron. In another embodiment, the thickness 138 of the mask 100 is about 8 micron. In another embodiment, the thickness 138 of the mask 100 is about 10 micron.

Thinner masks generally are more suitable for applications wherein the mask 100 is implanted at a relatively shallow location in (e.g., close to the anterior surface of) the cornea. In thinner masks, the body 104 may be sufficiently flexible such that it can take on the curvature of the structures with which it is coupled without negatively affecting the optical performance of the mask 100. In one application, the mask 100 is configured to be implanted about 5 um beneath the anterior surface of the cornea. In another application, the mask 100 is configured to be implanted about 52 um beneath the anterior surface of the cornea. In another application, the mask 100 is configured to be implanted about 125 um beneath the anterior surface of the cornea. Further details regarding implanting the mask 100 in the cornea are discussed above in connection with FIGS. 50A-51C.

A substantially planar mask has several advantages over a non-planar mask. For example, a substantially planar mask can be fabricated more easily than one that has to be formed to a particular curvature. In particular, the process steps involved in inducing curvature in the mask 100 can be eliminated. Also, a substantially planar mask may be more amenable to use on a wider distribution of the patient population (or among different sub-groups of a broader patient population) because the substantially planar mask uses the curvature of each patient's cornea to induce the appropriate amount of curvature in the body 104.

In some embodiments, the mask 100 is configured specifically for the manner and location of coupling with the eye. In particular, the mask 100 may be larger if applied over the eye as a contact lens or may be smaller if applied within the eye posterior of the cornea, e.g., proximate a surface of the lens of the eye. As discussed above, the thickness 138 of the body 104 of the mask 100 may be varied based on where the mask 100 is implanted. For implantation at deeper levels within the cornea, a thicker mask may be advantageous. Thicker masks are advantageous in some applications. For example, they are generally easier to handle, and therefore are easier to fabricate and to implant. Thicker masks may benefit more from having a preformed curvature than thinner masks. A thicker mask could be configured to have little or no curvature prior to implantation if it is configured to conform to the curvature of the native anatomy when applied.

The aperture 128 is configured to transmit substantially all incident light along the mask axis 136. The non-transmissive portion 132 surrounds at least a portion of the aperture 128 and substantially prevents transmission of incident light thereon. As discussed in connection with the above masks, the aperture 128 may be a through-hole in the body 104 or a substantially light transmissive (e.g., transparent) portion thereof. The aperture 128 of the mask 100 generally is defined within the outer periphery 124 of the mask 100. The aperture 128 may take any of suitable configurations, such as those described above in connection with FIGS. 6-42.

In one embodiment, the aperture 128 is substantially circular and is substantially centered in the mask 100. The size of the aperture 128 may be any size that is effective to increase the depth of focus of an eye of a patient suffering from presbyopia. For example, the aperture 128 can be circular, having a diameter of less than about 2.2 mm in one embodiment. In another embodiment, the diameter of the aperture is between about 1.8 mm and about 2.2 mm. In another embodiment, the aperture 128 is circular and has a diameter of about 1.8 mm or less. Most apertures will have a diameter within the range of from about 1.0 mm to about 2.5 mm, and often within the range of from about 1.3 mm to about 1.9 mm.

The non-transmissive portion 132 is configured to prevent transmission of radiant energy through the mask 100. For example, in one embodiment, the non-transmissive portion 132 prevents transmission of substantially all of at least a portion of the spectrum of the incident radiant energy. In one embodiment, the non-transmissive portion 132 is configured to prevent transmission of substantially all visible light, e.g., radiant energy in the electromagnetic spectrum that is visible to the human eye. The non-transmissive portion 132 may substantially prevent transmission of radiant energy outside the range visible to humans in some embodiments.

As discussed above in connection with FIG. 3, preventing transmission of light through the non-transmissive portion 132 decreases the amount of light that reaches the retina and the fovea that would not converge at the retina and fovea to form a sharp image. As discussed above in connection with FIG. 4, the size of the aperture 128 is such that the light transmitted therethrough generally converges at the retina or fovea. Accordingly, a much sharper image is presented to the eye than would otherwise be the case without the mask 100.

In one embodiment, the non-transmissive portion 132 prevents transmission of about 90 percent of incident light. In another embodiment, the non-transmissive portion 132 prevents transmission of about 92 percent of all incident light. The non-transmissive portion 132 of the mask 100 may be configured to be opaque to prevent the transmission of light. As used herein the term "opaque" is intended to be a broad term meaning capable of preventing the transmission of radiant energy, e.g., light energy, and also covers structures and arrangements that absorb or otherwise block all or less than all or at least a substantial portion of the light. In one embodiment, at least a portion of the body 104 is configured to be opaque to more than 99 percent of the light incident thereon.

As discussed above, the non-transmissive portion 132 may be configured to prevent transmission of light without absorbing the incident light. For example, the mask 100 could be made reflective or could be made to interact with the light in a more complex manner, as discussed in U.S. Pat. No. 6,551,424, issued Apr. 29, 2003, which is hereby incorporated by reference herein in its entirety.

As discussed above, the mask 100 also has a nutrient transport structure that in some embodiments comprises the plurality of holes 120. The presence of the plurality of holes 120 (or other transport structure) may affect the transmission of light through the non-transmissive portion 132 by potentially allowing more light to pass through the mask 100. In one embodiment, the non-transmissive portion 132 is configured to absorb about 99 percent or more of the incident light from passing through the mask 100 without holes 120 being present. The presence of the plurality of holes 120 allows more light to pass through the non-transmissive portion 132 such that only about 92 percent of the light incident on the non-transmissive portion 132 is prevented from passing through the non-transmissive portion 132. The holes 120 may reduce the benefit of the aperture 128 on the depth of focus of the eye by allowing more light to pass through the non-transmissive portion to the retina.

Reduction in the depth of focus benefit of the aperture 128 due to the holes 120 is balanced by the nutrient transmission benefits of the holes 120. In one embodiment, the transport structure 116 (e.g., the holes 120) is capable of substantially maintaining natural nutrient flow from a first corneal layer (i.e., one that is adjacent to the anterior surface 108 of the mask 100) to the second corneal layer (i.e., one that is adjacent to the posterior surface 112 of the mask 100). The plurality of holes 120 are configured to enable nutrients to pass through the mask 100 between the anterior surface 108 and the posterior surface 112. As discussed above, the holes 120 of the mask 100 shown in FIG. 43 may be located anywhere on the mask 100. Other mask embodiments described herein below locate substantially all of the nutrient transport structure in one or more regions of a mask.

The holes 120 of FIG. 43 extends at least partially between the anterior surface 108 and the posterior surface 112 of the mask 100. In one embodiment, each of the holes 120 includes a hole entrance 140 and a hole exit 164. The hole entrance 140 is located adjacent to the anterior surface 108 of the mask 100. The hole exit 164 is located adjacent to the posterior surface 112 of the mask 100. In one embodiment, each of the holes 120 extends the entire distance between the anterior surface 108 and the posterior surface 112 of the mask 100.

The transport structure 116 is configured to maintain the transport of one or more nutrients across the mask 100. The transport structure 116 of the mask 100 provides sufficient flow of one or more nutrients across the mask 100 to prevent depletion of nutrients at least at one of the first and second corneal layers (e.g., the layers 1210 and 1220). One nutrient of particular importance to the viability of the adjacent corneal layers is glucose. The transport structure 116 of the mask 100 provides sufficient flow of glucose across the mask 100 between the first and second corneal layers to prevent glucose depletion that would harm the adjacent corneal tissue. Thus, the mask 100 is capable of substantially maintaining nutrient flow (e.g., glucose flow) between adjacent corneal layers. In one embodiment, the nutrient transport structure 116 is configured to prevent depletion of more than about 4 percent of glucose (or other biological substance) in adjacent tissue of at least one of the first corneal layer and the second corneal layer.

The holes 120 may be configured to maintain the transport of nutrients across the mask 100. In one embodiment, the holes 120 are formed with a diameter of about 0.015 mm or more. In another embodiment, the holes have a diameter of about 0.020 mm. In another embodiment, the holes have a diameter of about 0.025 mm. In another embodiment, the holes 120 have a diameter in the range of about 0.020 mm to about 0.029 mm. The number of holes in the plurality of holes 120 is selected such that the sum of the surface areas of the hole entrances 140 of all the holes 100 comprises about 5 percent or more of surface area of the anterior surface 108 of the mask 100. In another embodiment, the number of holes 120 is selected such that the sum of the surface areas of the hole exits 164 of all the holes 120 comprises about 5 percent or more of surface area of the posterior surface 112 of the mask 100. In another embodiment, the number of holes 120 is selected such that the sum of the surface areas of the hole exits 164 of all the holes 120 comprises about 5 percent or more of surface area of the posterior surface 112 of the mask 112 and the sum of the surface areas of the hole entrances 140 of all the holes 120 comprises about 5 percent or more of surface area of the anterior surface 108 of the mask 100.

Each of the holes 120 may have a relatively constant cross-sectional area. In one embodiment, the cross-sectional shape of each of the holes 120 is substantially circular. Each of the holes 120 may comprise a cylinder extending between the anterior surface 108 and the posterior surface 112.

The relative position of the holes 120 is of interest in some embodiments. As discussed above, the holes 120 of the mask 100 are hex-packed, e.g., arranged in a hex pattern. In particular, in this embodiment, each of the holes 120 is separated from the adjacent holes 120 by a substantially constant distance, sometimes referred to herein as a hole pitch. In one embodiment, the hole pitch is about 0.045 mm.

In a hex pattern, the angles between lines of symmetry are approximately 43 degrees. The spacing of holes along any line of holes is generally within the range of from about 30 microns to about 100 microns, and, in one embodiment, is approximately 43 microns. The hole diameter is generally within the range of from about 10 microns to about 100 microns, and in one embodiment, is approximately 20 microns. The hole spacing and diameter are related if you want to control the amount of light coming through. The light transmission is a function of the sum of hole areas as will be understood by those of skill in the art in view of the disclosure herein.

The embodiment of FIG. 43 advantageously enables nutrients to flow from the first corneal layer to the second corneal layer. The inventors have discovered that negative visual effects can arise due to the presence of the transport structure 116. For example, in some cases, a hex packed arrangement of the holes 120 can generate diffraction patterns visible to the patient. For example, patients might observe a plurality of spots, e.g., six spots, surrounding a central light with holes 120 having a hex patterned.

The inventors have discovered a variety of techniques that produce advantageous arrangements of a transport structure such that diffraction patterns and other deleterious visual effects do not substantially inhibit other visual benefits of a mask. In one embodiment, where diffraction effects would be observable, the nutrient transport structure is arranged to spread the diffracted light out uniformly across the image to eliminate observable spots. In another embodiment, the nutrient transport structure employs a pattern that substantially eliminates diffraction patterns or pushes the patterns to the periphery of the image.

Figure 45A:
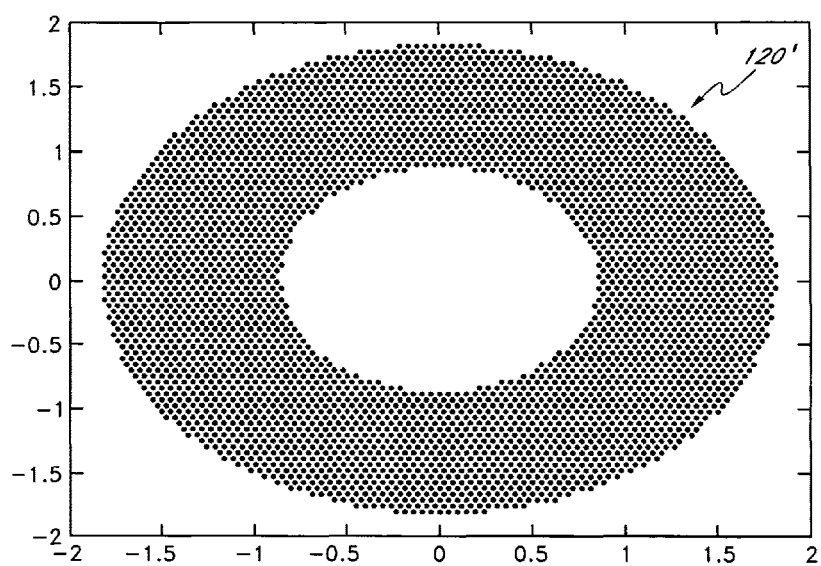
FIG. 45A is a graphical representation of one arrangement of holes of a plurality of holes that may be formed on the mask of FIG. 43.
Figure 45B:
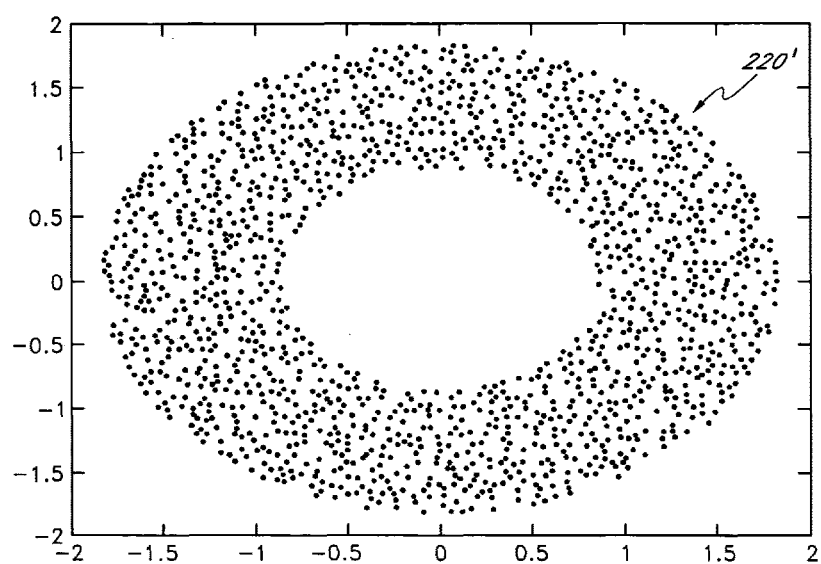
FIG. 45B is a graphical representation of another arrangement of holes of a plurality of holes that may be formed on the mask of FIG. 43.
Figure 45C:
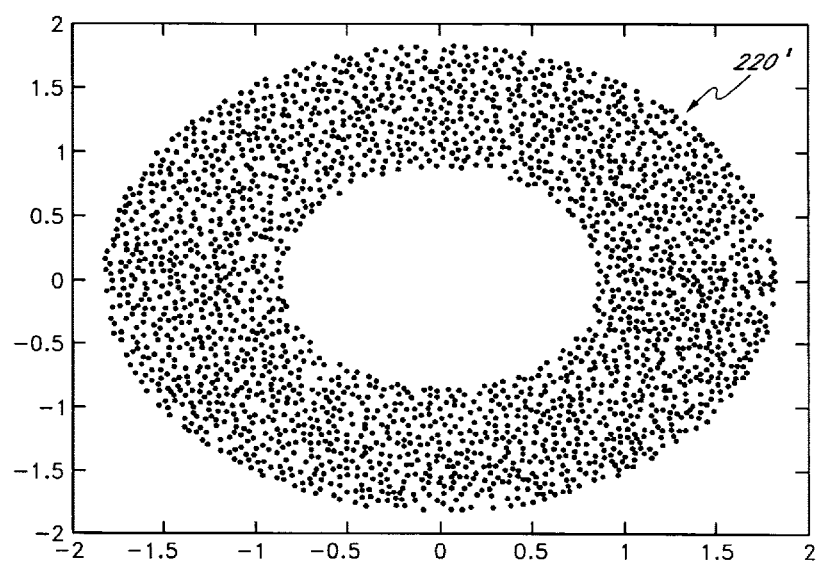
FIG. 45C is a graphical representation of another arrangement of holes of a plurality of holes that may be formed on the mask of FIG. 43.

FIG. 45B-45C show two embodiments of patterns of holes 220 that may be applied to a mask that is otherwise substantially similar to the mask 100. The holes 220 of the hole patterns of FIGS. 45A-45B are spaced from each other by a random hole spacing or hole pitch. In other embodiments discussed below, holes are spaced from each other by a non-uniform amount, e.g., not a random amount. In one embodiment, the holes 220 have a substantially uniform shape (cylindrical shafts having a substantially constant cross-sectional area). FIG. 45C illustrates a plurality of holes 220 separated by a random spacing, wherein the density of the holes is greater than that of FIG. 45B. Generally, the higher the percentage of the mask body that has holes the more the mask will transport nutrients in a manner similar to the native tissue. One way to provide a higher percentage of hole area is to increase the density of the holes. Increased hole density can also permit smaller holes to achieve the same nutrient transport as is achieved by less dense, larger holes.

Figure 46A:
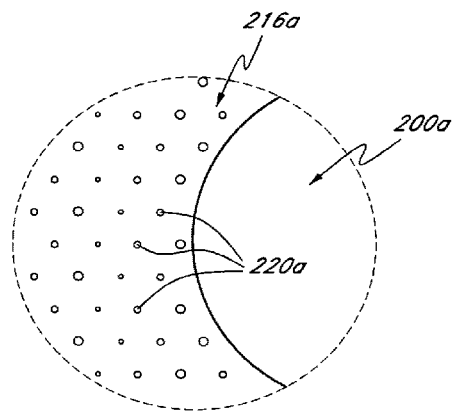
FIG. 46A is an enlarged view similar to that of FIG. 43A showing a variation of a mask having non-uniform size.

FIG. 46A shows a portion of another mask 200a that is substantially similar to the mask 100, except described differently below. The mask 200a can be made of the materials discussed herein, including those discussed in Section III. The mask 200a can be formed by any suitable process, such as those discussed below in connection with FIGS. 48a-48d and with variations of such processes. The mask 200a has a nutrient transport structure 216a that includes a plurality of holes 220a. A substantial number of the holes 220a have a non-uniform size. The holes 220a may be uniform in cross-sectional shape. The cross-sectional shape of the holes 220a is substantially circular in one embodiment. The holes 220a may be circular in shape and have the same diameter from a hole entrance to a hole exit, but are otherwise non-uniform in at least one aspect, e.g., in size. It may be preferable to vary the size of a substantial number of the holes by a random amount. In another embodiment, the holes 220a are non-uniform (e.g., random) in size and are separated by a non-uniform (e.g., a random) spacing.

Figure 46B:
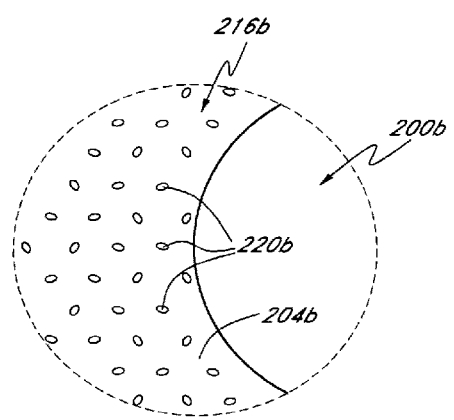
FIG. 46B is an enlarged view similar to that of FIG. 43A showing a variation of a mask having a non-uniform facet orientation.

FIG. 46B illustrates another embodiment of a mask 200b that is substantially similar to the mask 100, except as described differently below. The mask 200b can be made of the materials discussed herein, including those discussed in Section III. Also, the mask 200b can be formed by any suitable process, such as those discussed below in connection with FIGS. 48a-48d and with variations of such processes. The mask 200b includes a body 204b. The mask 200b has a transport structure 216b that includes a plurality of holes 220b with a non-uniform facet orientation. In particular, each of the holes 220b has a hole entrance that may be located at an anterior surface of the mask 200b. A facet of the hole entrance is defined by a portion of the body 204b of the mask 200b surrounding the hole entrance. The facet is the shape of the hole entrance at the anterior surface. In one embodiment, most or all the facets have an elongate shape, e.g., an oblong shape, with a long axis and a short axis that is perpendicular to the long axis. The facets may be substantially uniform in shape. In one embodiment, the orientation of facets is not uniform. For example, a substantial number of the facets may have a non-uniform orientation. In one arrangement, a substantial number of the facets have a random orientation. In some embodiments, the facets are non-uniform (e.g., random) in shape and are non-uniform (e.g., random) in orientation.

Other embodiments may be provided that vary at least one aspect, including one or more of the foregoing aspects, of a plurality of holes to reduce the tendency of the holes to produce visible diffraction patterns or patterns that otherwise reduce the vision improvement that may be provided by a mask with an aperture, such as any of those described above. For example, in one embodiment, the hole size, shape, and orientation of at least a substantial number of the holes may be varied randomly or may be otherwise non-uniform.

Figure 47:
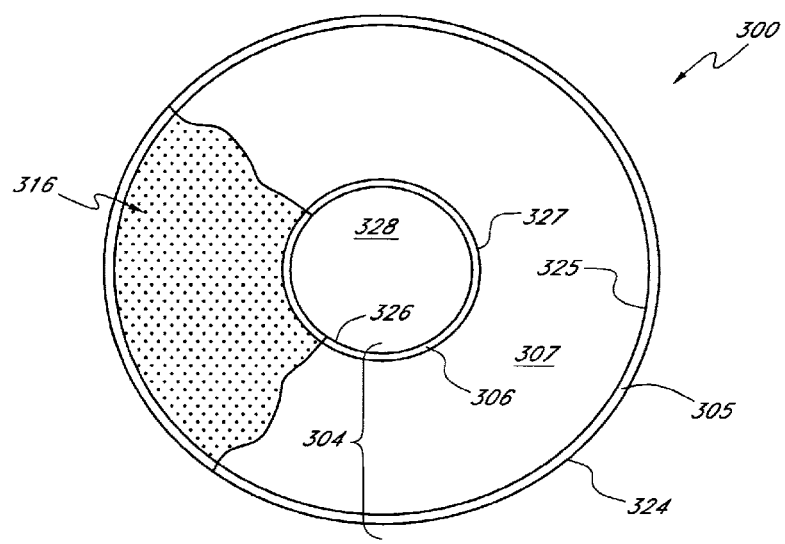
FIG. 47 is a top view of another embodiment of a mask having a hole region and a peripheral region.

FIG. 47 shows another embodiment of a mask 300 that is substantially similar to any of the masks hereinbefore described, except as described differently below. The mask 300 can be made of the materials discussed herein, including those discussed in Section III. Also, the mask 300 can be formed by any suitable process, such as those discussed below in connection with FIGS. 48a-48d and with variations of such processes. The mask 300 includes a body 304. The body 304 has an outer peripheral region 305, an inner peripheral region 306, and a hole region 307. The hole region 307 is located between the outer peripheral region 305 and the inner peripheral region 306. The body 304 may also include an aperture region, where the aperture (discussed below) is not a through hole. The mask 300 also includes a nutrient transport structure 316. In one embodiment, the nutrient transport structure includes a plurality of holes. At least a substantial portion of the holes (e.g., all of the holes) are located in the hole region 307. As above, only a portion of the nutrient structure 316 is shown for simplicity. But it should be understood that the holes may be located through the hole region 307.

The outer peripheral region 305 may extend from an outer periphery 324 of the mask 300 to a selected outer circumference 326 of the mask 300. The selected outer circumference 325 of the mask 300 is located a selected radial distance from the outer periphery 324 of the mask 300. In one embodiment, the selected outer circumference 325 of the mask 300 is located about 0.05 mm from the outer periphery 324 of the mask 300.

The inner peripheral region 306 may extend from an inner location, e.g., an inner periphery 326 adjacent an aperture 328 of the mask 300 to a selected inner circumference 327 of the mask 300. The selected inner circumference 327 of the mask 300 is located a selected radial distance from the inner periphery 326 of the mask 300. In one embodiment, the selected inner circumference 327 of the mask 300 is located about 0.05 mm from the inner periphery 326.

The mask 300 may be the product of a process that involves random selection of a plurality of locations and formation of holes on the mask 300 corresponding to the locations. As discussed further below, the method can also involve determining whether the selected locations satisfy one or more criteria. For example, one criterion prohibits all, at least a majority, or at least a substantial portion of the holes from being formed at locations that correspond to the inner or outer peripheral regions 305, 306. Another criterion prohibits all, at least a majority, or at least a substantial portion of the holes from being formed too close to each other. For example, such a criterion could be used to assure that a wall thickness, e.g., the shortest distance between adjacent holes, is not less than a predetermined amount. In one embodiment, the wall thickness is prevented from being less than about 20 microns.

In a variation of the embodiment of FIG. 47, the outer peripheral region 305 is eliminated and the hole region 307 extends from the inner peripheral region 306 to an outer periphery 324. In another variation of the embodiment of FIG. 47, the inner peripheral region 306 is eliminated and the hole region 307 extends from the outer peripheral region 305 to an inner periphery 326.

Figure 44B:
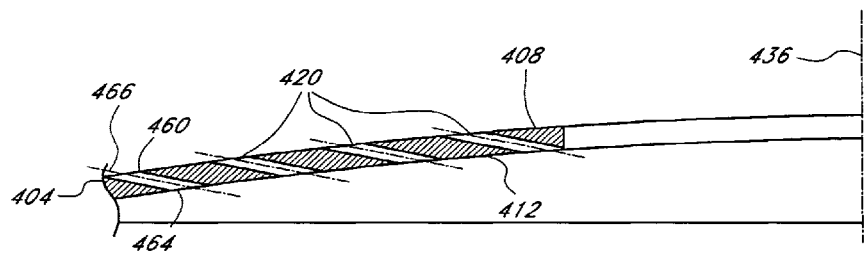
FIG. 44B is a cross-sectional view similar to FIG. 44A of another embodiment of a mask.

FIG. 44B shows a mask 400 that is similar to the mask 100 except as described differently below. The mask 400 can be made of the materials discussed herein, including those discussed in Section III. The mask 400 can be formed by any suitable process, such as those discussed below in connection with FIGS. 48a-48d and with variations of such processes. The mask 400 includes a body 404 that has an anterior surface 408 and a posterior surface 412. The mask 400 also includes a nutrient transport structure 4316 that, in one embodiment, includes a plurality of holes 420. The holes 420 are formed in the body 404 so that nutrient transport is provided but transmission of radiant energy (e.g., light) to the retinal locations adjacent the fovea through the holes 404 is substantially prevented. In particular, the holes 404 are formed such that when the eye with which the mask 1000 is coupled is directed at an object to be viewed, light conveying the image of that object that enters the holes 420 cannot exit the holes along a path ending near the fovea.

In one embodiment, each of the holes 420 has a hole entrance 460 and a hole exit 464. Each of the holes 420 extends along a transport axis 466. The transport axis 466 is formed to substantially prevent propagation of light from the anterior surface 408 to the posterior surface 412 through the holes 420. In one embodiment, at least a substantial number of the holes 420 have a size to the transport axis 466 that is less than a thickness of the mask 400. In another embodiment, at least a substantial number of the holes 420 have a longest dimension of a perimeter at least at one of the anterior or posterior surfaces 408, 412 (e.g., a facet) that is less than a thickness of the mask 400. In some embodiments, the transport axis 466 is formed at an angle with respect to a mask axis 436 that substantially prevents propagation of light from the anterior surface 408 to the posterior surface 412 through the hole 420. In another embodiment, the transport axis 466 of one or more holes 420 is formed at an angle with respect to the mask axis 436 that is large enough to prevent the projection of most of the hole entrance 460 from overlapping the hole exit 464.

In one embodiment, the hole 420 is circular in cross-section and has a diameter between about 0.5 micron and about 8 micron and the transport axis 466 is between 5 and 85 degrees. The length of each of the holes 420 (e.g., the distance between the anterior surface 408 and the posterior surface 412) is between about 8 and about 92 micron. In another embodiment, the diameter of the holes 420 is about 5 micron and the transport angle is about 40 degrees or more. As the length of the holes 420 increases it may be desirable to include additional holes 420. In some cases, additional holes 420 counteract the tendency of longer holes to reduce the amount of nutrient flow through the mask 400.

Figure 44C:
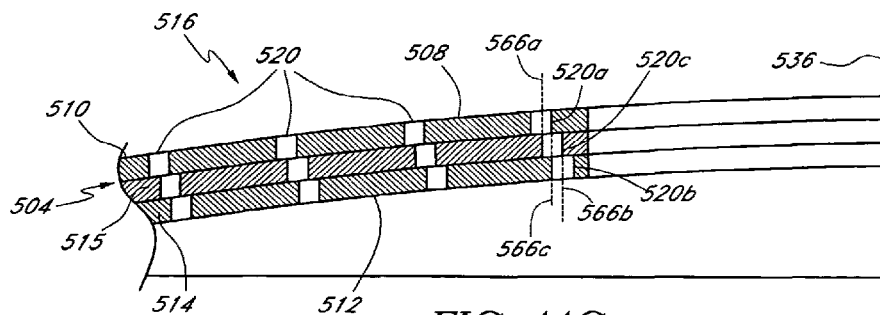
FIG. 44C is a cross-sectional view similar to FIG. 44A of another embodiment of a mask.

FIG. 44C shows another embodiment of a mask 500 similar to the mask 100, except as described differently below. The mask 500 can be made of the materials discussed herein, including those discussed in Section III. The mask 500 can be formed by any suitable process, such as those discussed below in connection with FIGS. 48a-48d and with variations of such processes. The mask 500 includes a body 504 that has an anterior surface 508, a first mask layer 510 adjacent the anterior surface 508, a posterior surface 512, a second mask layer 514 adjacent the posterior surface 512, and a third mask layer 515 located between the first mask layer 510 and the second mask layer 514. The mask 500 also includes a nutrient transport structure 516 that, in one embodiment, includes a plurality of holes 520. The holes 520 are formed in the body 504 so that nutrient are transported across the mask, as discussed above, but transmission of radiant energy (e.g., light) to retinal locations adjacent the fovea through the holes 520 is substantially prevented. In particular, the holes 520 are formed such that when the eye with which the mask 500 is coupled is directed at an object to be viewed, light conveying the image of that object that enters the holes 520 cannot exit the holes along a path ending near the fovea.

In one embodiment, at least one of the holes 520 extends along a non-linear path that substantially prevents propagation of light from the anterior surface to the posterior surface through the at least one hole. In one embodiment, the mask 500 includes a first hole portion 520a that extends along a first transport axis 566a, the second mask layer 514 includes a second hole portion 520b extending along a second transport axis 566b, and the third mask layer 515 includes a third hole portion 520c extending along a third transport axis 566c. The first, second, and third transport axes 566a, 566b, 566c preferably are not collinear. In one embodiment, the first and second transport axes 566a, 566b are parallel but are off-set by a first selected amount. In one embodiment, the second and third transport axes 566b, 566c are parallel but are off-set by a second selected amount. In the illustrated embodiment, each of the transport axes 566a, 566b, 566c are off-set by one-half of the width of the hole portions 520a, 520b, 520c. Thus, the inner-most edge of the hole portion 520a is spaced from the axis 536 by a distance that is equal to or greater than the distance of the outer-most edge of the hole portion 520b from the axis 536. This spacing substantially prevents light from passing through the holes 520 from the anterior surface 508 to the posterior surface 512.

In one embodiment, the first and second amounts are selected to substantially prevent the transmission of light therethrough. The first and second amounts of off-set may be achieved in any suitable fashion. One technique for forming the hole portions 520a, 520b, 520c with the desired off-set is to provide a layered structure. As discussed above, the mask 500 may include the first layer 510, the second layer 514, and the third layer 515. FIG. 44C shows that the mask 500 can be formed with three layers. In another embodiment, the mask 500 is formed of more than three layers. Providing more layers may advantageously further decrease the tendency of light to be transmitted through the holes 490 onto the retina. This has the benefit of reducing the likelihood that a patient will observe or otherwise perceive a pattern that will detract from the vision benefits of the mask 500. A further benefit is that less light will pass through the mask 500, thereby enhancing the depth of focus increase due to the pin-hole sized aperture formed therein.

In any of the foregoing mask embodiments, the body of the mask may be formed of a material selected to provide adequate nutrient transport and to substantially prevent negative optic effects, such as diffraction, as discussed above. In various embodiments, the masks are formed of an open cell foam material. In another embodiment, the masks are formed of an expanded solid material.

As discussed above in connection with FIGS. 45B and 45C, various random patterns of holes may advantageously be provided for nutrient transport. In some embodiment, it may be sufficient to provide regular patterns that are non-uniform in some aspect. Non-uniform aspects to the holes may be provided by any suitable technique.

In a first step of one technique, a plurality of locations 220' is generated. The locations 220' are a series of coordinates that may comprise a non-uniform pattern or a regular pattern. The locations 220' may be randomly generated or may be related by a mathematical relationship (e.g., separated by a fixed spacing or by an amount that can be mathematically defined). In one embodiment, the locations are selected to be separated by a constant pitch or spacing and may be hex packed.

In a second step, a subset of the locations among the plurality of locations 220' is modified to maintain a performance characteristic of the mask. The performance characteristic may be any performance characteristic of the mask. For example, the performance characteristic may relate to the structural integrity of the mask. Where the plurality of locations 220' is selected at random, the process of modifying the subset of locations may make the resulting pattern of holes in the mask a "pseudo-random" pattern.

Where a hex packed pattern of locations (such as the locations 120' of FIG. 45A) is selected in the first step, the subset of locations may be moved with respect to their initial positions as selected in the first step. In one embodiment, each of the locations in the subset of locations is moved by an amount equal to a fraction of the hole spacing. For example, each of the locations in the subset of locations may be moved by an amount equal to one-quarter of the hole spacing. Where the subset of locations is moved by a constant amount, the locations that are moved preferably are randomly or pseudo-randomly selected. In another embodiment, the subset of location is moved by a random or a pseudo-random amount.

In one technique, an outer peripheral region is defined that extends between the outer periphery of the mask and a selected radial distance of about 0.05 mm from the outer periphery. In another embodiment, an inner peripheral region is defined that extends between an aperture of the mask and a selected radial distance of about 0.05 mm from the aperture. In another embodiment, an outer peripheral region is defined that extends between the outer periphery of the mask and a selected radial distance and an inner peripheral region is defined that extends between the aperture of the mask and a selected radial distance from the aperture. In one technique, the subset of location is modified by excluding those locations that would correspond to holes formed in the inner peripheral region or the outer peripheral region. By excluding locations in at least one of the outer peripheral region and the inner peripheral region, the strength of the mask in these regions is increased. Several benefits are provided by stronger inner and outer peripheral regions. For example, the mask may be easier to handle during manufacturing or when being applied to a patient without causing damage to the mask.

In another embodiment, the subset of locations is modified by comparing the separation of the holes with minimum and/or maximum limits. For example, it may be desirable to assure that no two locations are closer than a minimum value. In some embodiments this is important to assure that the wall thickness, which corresponds to the separation between adjacent holes, is no less than a minimum amount. As discussed above, the minimum value of separation is about 20 microns in one embodiment, thereby providing a wall thickness of no less than about 20 microns.

In another embodiment, the subset of locations is modified and/or the pattern of location is augmented to maintain an optical characteristic of the mask. For example, the optical characteristic may be opacity and the subset of locations may be modified to maintain the opacity of a non-transmissive portion of a mask. In another embodiment, the subset of locations may be modified by equalizing the density of holes in a first region of the body compared with the density of holes in a second region of the body. For example, the locations corresponding to the first and second regions of the non-transmissive portion of the mask may be identified. In one embodiment, the first region and the second region are arcuate regions (e.g., wedges) of substantially equal area. A first areal density of locations (e.g., locations per square inch) is calculated for the locations corresponding to the first region and a second areal density of locations is calculated for the locations corresponding to the second region. In one embodiment, at least one location is added to either the first or the second region based on the comparison of the first and second areal densities. In another embodiment, at least one location is removed based on the comparison of the first and second areal densities.

The subset of locations may be modified to maintain nutrient transport of the mask. In one embodiment, the subset of location is modified to maintain glucose transport.

In a third step, a hole is formed in a body of a mask at locations corresponding to the pattern of locations as modified, augmented, or modified and augmented. The holes are configured to substantially maintain natural nutrient flow from the first layer to the second layer without producing visible diffraction patterns.

V. Methods of Applying Pinhole Aperture Devices

The various masks discussed herein can be used to improve the vision of a presbyopic patient as well as patient's with other vision problems. The masks discussed herein can be deployed in combination with a LASIK procedure, to eliminate the effects of abrasions, aberrations, and divots in the cornea. It is also believed that the masks disclosed herein can be used to treat patients suffering from macular degeneration, e.g., by directing light rays to unaffected portions of retina, thereby improving the vision of the patient. Whatever treatment is contemplated, more precise alignment of the central region of a mask that has a pin-hole aperture with the line of sight or visual axis of the patient is believed to provide greater clinical benefit to the patient. Other ocular devices that do not require a pin-hole aperture can also benefit from the alignment techniques discussed below. Also, various structures and techniques that can be used to remove an ocular devices are discussed below.

A. Alignment of the Pinhole Aperture with the Patient's Visual Axis

Alignment of the central region of the pinhole aperture 38, in particular, the optical axis 39 of the mask 34 with the visual axis of the eye 10 may be achieved in a variety of ways. In one technique, an optical device employs input from the patient to locate the visual axis in connection with a procedure to implant the mask 34. This technique is described in more detail in U.S. patent application Ser. No. 11/000,562, filed Dec. 1, 2004, the entire contents of which is hereby expressly incorporated by reference herein.

In other embodiments, systems and methods identify one or more visible ocular features that correlate to the line of sight. The one or more visible ocular feature(s) is observed while the mask is being applied to the eye. Alignment using a visible ocular feature enables the mask to perform adequately to increase depth of focus. In some applications, a treatment method enhances the correlation of the visible ocular feature and the line of sight to maintain or improve alignment of the mask axis and the line of sight.

Accurate alignment of the mask is believed to improve the clinical benefit of the mask. However, neither the optical axis of the mask nor the line of sight of the patient is generally visible during the surgical procedures contemplated for implanting masks. However, substantial alignment of the optical axis of the mask and the line of sight may be achieved by aligning a visible feature of the mask with a visible feature of the eye, e.g., a visible ocular feature. As used herein, the term "visible ocular feature" is a broad term that includes features viewable with a viewing aid, such as a surgical microscope or loupes, as well as those visible to the unaided eye. Various methods are discussed below that enhance the accuracy of the placement of the mask using a visible ocular feature. These methods generally involve treating the eye to increase the correlation between the location of the visible ocular feature and the line of sight or to increase the visibility of the ocular feature.

Figure 48:
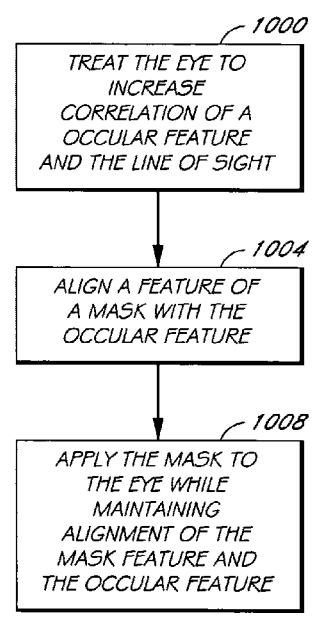
FIG. 48 is a flow chart illustrating one method of aligning a mask with an axis of the eye based on observation of an anatomical feature of the eye.

FIG. 48 is a flow chart illustrating one method of aligning a mask with an axis of the eye using a visible ocular feature. The method may include a step of identifying a visible ocular feature, a combination of visible ocular features, or a combination of a visible ocular feature and an optical effect that sufficiently correlate with the location of the line of sight of the eye. In one technique the entrance pupil or other visible ocular feature could be used alone to estimate the location of the line of sight. In another technique, the location of the line of sight can be estimated to be located between, e.g., half-way between, the center of the entrance pupil and the first Purkinje image. Other estimates can be based on a combination of two or more of the first Purkinje image, the second Purkinje image, the third Purkinje image, and the fourth Purkinje image. Other estimates can be based on one or more Purkinje image and one or more other anatomical features. In another technique, the location of the line of sight can be estimated as being located at the center of the pupil if the first Purkinje image is located close to the center of the entrance pupil. A single Purkinje image may provide an adequate estimate of the location of the line of sight if the Purkinje image is generated by a beam having a fixed or a know angle of incidence relative to a surface of the eye. The method may also include a step of identifying a visible feature of the mask to be aligned with a visible ocular feature, as discussed further below.

In a step 1000, an eye is treated to affect or alter, preferably temporarily, a visible ocular feature. In some embodiments, the feature of the eye is altered to increase the correlation of the location of the ocular feature to the line of sight of the eye. In some cases, the treatment of step 1000 enhances the visibility of the ocular feature to the surgeon. The ocular feature may be any suitable feature, such as the pupil or any other feature that correlates or can be altered by a treatment to correlate with the line of sight of the patient. Some techniques involve the alignment of a feature of a mask with the pupil or a portion of the pupil. One technique for enhancing the visibility of the pupil or the correlation of the location of the pupil with the line of sight involves manipulating the size of the pupil, e.g., increasing or decreasing the pupil size.

In connection with the method of FIG. 48, any suitable criteria can be used to confirm alignment of an eye and a mask with a pin-hole aperture. For example, the mask can be considered aligned with the eye when any feature of the mask is aligned with any anatomical landmark on the eye so that an axis passing through the center of the pin-hole aperture is co-linear with or substantially co-linear with an optical axis of the eye, such as the line of sight and an axis passing through the center of the entrance pupil and the center of the eyeball. As used herein, "anatomical landmark" is a broad term that includes an visible ocular feature, such as the center of the entrance pupil, the intersection of the line of sight with a selected corneal layer, the inner periphery of the iris, the outer periphery of the iris, the inner periphery of the sclera, the boundary between the iris and the pupil, the boundary between the iris and the sclera, the location of the first Purkinje image, the location of the second Purkinje image, the location of the third Purkinje image, the location of the fourth Purkinje image, the relative position of any combination of Purkinje images, the combination of the location of a Purkinje image and any other anatomical landmark, and any combination of the foregoing or other anatomical feature.

The pupil size may be decreased by any suitable technique, including pharmacologic manipulation and light manipulation. One agent used in pharmacologic manipulation of pupil size is pilocarpine. Pilocarpine reduces the size of the pupil when applied to the eye. One technique for applying pilocarpine is to inject an effective amount into the eye. Other agents for reducing pupil size include: carbachol, demecarium, isoflurophate, physostigmine, aceclidine, and echothiophate.

Pilocarpine is known to shift the location of the pupil nasally in some cases. This can be problematic for some ocular procedures, e.g., those procedures directed at improving distance vision. The applicant has discovered, however, that such a shift does not significantly reduce the efficacy of the masks described herein.

While the alignment of the masks described herein with the line of sight is not significantly degraded by the use of pilocarpine, an optional step of correcting for the nasal shift of the pupil may be performed.

In one variation, the treatment of the step 1000 involves increasing pupil size. This technique may be more suitable where it is desired to align a visible mask feature near an outer periphery of the mask with the pupil. These techniques are discussed further below.

As discussed above, the treatment of the step 1000 can involve non-pharmacologic techniques for manipulating a visible ocular feature. One non-pharmacologic technique involves the use of light to cause the pupil size to change. For example, a bright light can be directed into the eye to cause the pupil to constrict. This approach may substantially avoid displacement of the pupil that has been observed in connection with some pharmacologic techniques. Light can also be used to increase pupil size. For example, the ambient light can be reduced to cause the pupil to dilate. A dilated pupil may provide some advantages in connection with aligning to a visible mask feature adjacent to an outer periphery of a mask, as discussed below.

In a step 1004, a visible feature of a mask is aligned with the ocular feature identified in connection with step 1000. As discussed above, the mask may have an inner periphery, an outer periphery, and a pin-hole aperture located within the inner periphery. The pin-hole aperture may be centered on a mask axis. Other advantageous mask features discussed above may be included in masks applied by the methods illustrated by FIG. 48. For example, such features may include nutrient transport structures configured to substantially eliminate diffraction patterns, structures configured to substantially prevent nutrient depletion in adjacent corneal tissue, and any other mask feature discussed above in connection with other masks.

One technique involves aligning at least a portion of the inner periphery of a mask with an anatomical landmark. For example, the inner periphery of the mask could be aligned with the inner periphery of the iris. This may be accomplished using unaided vision or a viewing aid, such as loupes or a surgical microscope. The mask could be aligned so that substantially the same spacing is provided between the inner periphery of the mask and the inner periphery of the iris. This technique could be facilitated by making the iris constrict, as discussed above. A viewing aid may be deployed to further assist in aligning the mask to the anatomical landmark. For example, a viewing aid could include a plurality of concentric markings that the surgeon can use to position the mask. Where the inner periphery of the iris is smaller than the inner periphery of the mask, a first concentric marking can be aligned with the inner periphery of the iris and the mask could be positioned so that a second concentric marking is aligned with the inner periphery of the mask. The second concentric marking would be farther from the common center than the first concentric marking in this example.

In another technique, the outer periphery of the mask could be aligned with an anatomical landmark, such as the inner periphery of the iris. This technique could be facilitated by dilating the pupil. This technique may be enhanced by the use of a viewing aid, which could include a plurality of concentric markings, as discussed above. In another technique, the outer periphery of the mask could be aligned with an anatomical landmark, such as the boundary between the iris and the sclera. This technique may be facilitated by the use of a viewing aid, such as a plurality of concentric markings.

In another technique, the mask can be aligned so that substantially the same spacing is provided between the inner periphery of the mask and the inner periphery of the iris. In this technique, the pupil preferably is constricted so that the diameter of the pupil is less than the diameter of the pin-hole aperture.

Alternatively, an artifact can be formed in the mask that gives a visual cue of proper alignment. For example, there could be one or more window portions formed in the mask through which the edge of the pupil could be observed. The window portions could be clear graduations or they could be at least partially opaque regions through which the pupil could be observed. In one technique, the surgeon moves the mask until the pupil can be seen in corresponding window portions on either side of the pin-hole aperture. The window portions enable a surgeon to align a visible ocular feature located beneath a non-transparent section of the mask with a feature of the mask. This arrangement enables alignment without a great amount of pupil constriction, e.g., where the pupil is not fully constricted to a size smaller than the diameter of the inner periphery.

Preferably the alignment of the ocular feature with one or more visible mask features causes the mask axis to be substantially aligned with the line of sight of the eye. "Substantial alignment" of the mask axis with the eye, e.g., with the line of sight of the eye (and similar terms, such as "substantially collinear") can be said to have been achieved when a patient's vision is improved by the implantation of the mask. In some cases, substantial alignment can be said to have been achieved when the mask axis is within a circle centered on the line of sight and having a radius no more than 5 percent of the radius of the inner periphery of the mask. In some cases, substantial alignment can be said to have been achieved when the mask axis is within a circle centered on the line of sight and having a radius no more than 10 percent of the radius of the inner periphery of the mask. In some cases, substantial alignment can be said to have been achieved when the mask axis is within a circle centered on the line of sight and having a radius no more than 15 percent of the radius of the inner periphery of the mask. In some cases, substantial alignment can be said to have been achieved when the mask axis is within a circle centered on the line of sight and having a radius no more than 20 percent of the radius of the inner periphery of the mask. In some cases, substantial alignment can be said to have been achieved when the mask axis is within a circle centered on the line of sight and having a radius no more than 25 percent of the radius of the inner periphery of the mask. In some cases, substantial alignment can be said to have been achieved when the mask axis is within a circle centered on the line of sight and having a radius no more than 30 percent of the radius of the inner periphery of the mask. As discussed above, the alignment of the mask axis and the line of sight of the patient is believed to enhance the clinical benefit of the mask.

In a step 1008, the mask is applied to the eye of the patient. Preferably the alignment of the optical axis of the mask and the line of sight of the patient is maintained while the mask is applied to the eye of the patient. In some cases, this alignment is maintained by maintaining the alignment of a mask feature, e.g., a visible mask feature, and a pupil feature, e.g., a visible pupil feature. For example, one technique maintains the alignment of at least one of the inner periphery and the outer periphery of the mask and the pupil while the mask is being applied to the eye of the patient.

As discussed above, a variety of techniques are available for applying a mask to the eye of a patient. Any suitable technique of applying a mask may be employed in connection with the method illustrated in FIG. 48. For example, as set forth above in connection with FIGS. 50A-51C, various techniques may be employed to position the mask at different depths or between different layers within the cornea. In particular, in one technique, a corneal flap of suitable depth is hinged open. The depth of the flap is about the outermost 20% of the thickness of the cornea in one technique. In another technique, the depth of the flap is about the outermost 10% of the thickness of the cornea. In another technique, the depth of the flap is about the outermost 5% of the thickness of the cornea. In another technique, the depth of the flap is in the range of about the outermost 5% to about the outermost 10% of the thickness of the cornea. In another technique, the depth of the flap is in the range of about the outermost 5% to about the outermost 20% of the thickness of the cornea. Other depths and ranges are possible for other techniques.

Thereafter, in one technique, the mask is placed on a layer of the cornea such that at least one of the inner periphery and the outer periphery of the mask is at a selected position relative to the pupil. In variations on this technique, other features of the mask may be aligned with other ocular features. Thereafter, the hinged corneal flap is placed over the mask.

Additional techniques for applying a mask are discussed above in connection with FIGS. 52A-53. These methods may be modified for use in connection with alignment using visible features. These techniques enable the mask to be initially placed on the corneal layer that is lifted from the eye. The initial placement of the mask on the lifted corneal layer may be before or after alignment of a visible ocular feature with a visible mask feature. In some techniques, primary and secondary alignment steps are performed before and after the initial placement of the mask on the lifted corneal layer.

Many additional variations of the foregoing methods are also possible. The alignment methods involving alignment of visible features may be combined with any of the techniques discussed above in connection with optically locating the patient's line of sight. One technique involves removing an epithelial sheet and creating a depression in the Bowman's membrane or in the stroma. Also, the mask can be placed in a channel formed in the cornea, e.g., in or near the top layers of the stroma. Another useful technique for preparing the cornea involves the formation of a pocket within the cornea. These methods related to preparation of the cornea are described in greater detail above.

Some techniques may benefit from the placement of a temporary post-operative covering, such as a contact lens or other covering, over the flap until the flap has healed. In one technique, a covering is placed over the flap until an epithelial sheet adheres to the mask or grows over an exposed layer, such as the Bowman's membrane.

B. Methods of Applying a Mask

Having described method for locating the visual axis of the eye 10 or a visible ocular feature that indicates the location thereof, and for visually marking the visual axis, various methods for applying a mask to the eye will be discussed.

Figure 49:
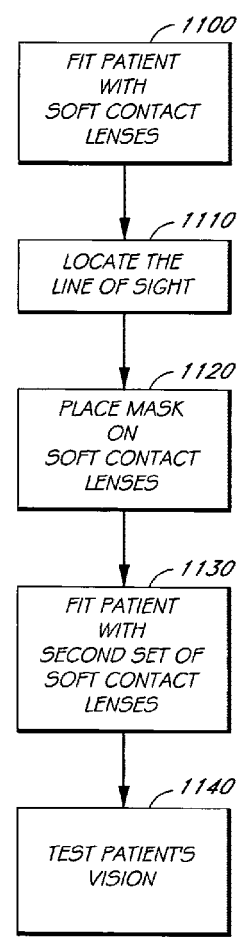
FIG. 49 is a flow chart illustrating one method of screening a patient for the use of a mask.

FIG. 49 shows one technique for screening a patient interested in increasing his or her depth of focus. The process begins at step 1100, in which the patient is fitted with soft contact lenses, i.e., a soft contact lens is placed in each of the patient's eyes. If needed, the soft contact lenses may include vision correction. Next, at step 1110, the visual axis of each of the patient's eyes is located as described above. At a step 1120, a mask, such as any of those described above, is placed on the soft contact lenses such that the optical axis of the aperture of the mask is aligned with the visual axis of the eye. In this position, the mask will be located generally concentric with the patient's pupil. In addition, the curvature of the mask should parallel the curvature of the patient's cornea. The process continues at a step 1130, in which the patient is fitted with a second set of soft contact lenses, i.e., a second soft contact lens is placed over the mask in each of the patient's eyes. The second contact lens holds the mask in a substantially constant position. Last, at step 1140, the patient's vision is tested. During testing, it is advisable to check the positioning of the mask to ensure that the optical axis of the aperture of the mask is substantially collinear with the visual axis of the eye. Further details of testing are set forth in U.S. Pat. No. 6,551,424, issued Apr. 29, 2003, incorporated by reference herein in its entirety.

In accordance with a still further embodiment of the invention, a mask is surgically implanted into the eye of a patient interested in increasing his or her depth of focus. For example, a patient may suffer from presbyopia, as discussed above. The mask may be a mask as described herein, similar to those described in the prior art, or a mask combining one or more of these properties. Further, the mask may be configured to correct visual aberrations. To aid the surgeon surgically implanting a mask into a patient's eye, the mask may be pre-rolled or folded for ease of implantation.

The mask may be implanted in several locations. For example, the mask may be implanted underneath the cornea's epithelium sheet, beneath the cornea's Bowman membrane, in the top layer of the cornea's stroma, or in the cornea's stroma. When the mask is placed underneath the cornea's epithelium sheet, removal of the mask requires little more than removal of the cornea's epithelium sheet.

Figure 50A:
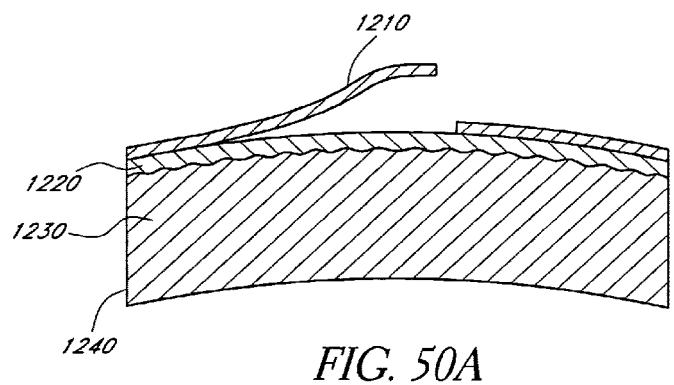
FIGS. 50A-50C show a mask, similar to those described herein, inserted beneath an epithelium sheet of a cornea.
Figure 50B:
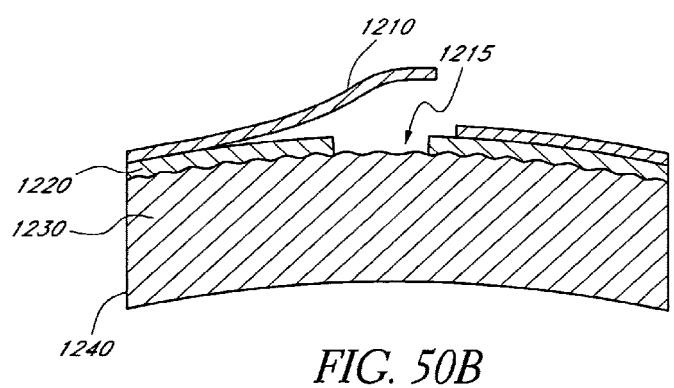
Figure 50C:
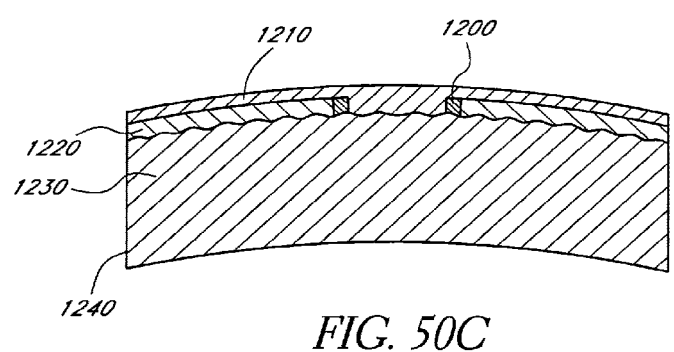

FIGS. 50a through 50c show a mask 1200 inserted underneath an epithelium sheet 1210. In this embodiment, the surgeon first removes the epithelium sheet 1210. For example, as shown in FIG. 50a, the epithelium sheet 1210 may be rolled back. Then, as shown in FIG. 50b, the surgeon creates a depression 1215 in a Bowman's membrane 420 corresponding to the visual axis of the eye. The visual axis of the eye may be located as described above and may be marked by use of the alignment apparatus 1200 or other similar apparatus. The depression 1215 should be of sufficient depth and width to both expose the top layer 1230 of the stroma 1240 and to accommodate the mask 1200. The mask 1200 is then placed in the depression 1215. Because the depression 1215 is located in a position to correspond to the visual axis of the patient's eye, the central axis of the pinhole aperture of the mask 1200 will be substantially collinear with the visual axis of the eye. This will provide the greatest improvement in vision possible with the mask 1200. Last, the epithelium sheet 1210 is placed over the mask 1200. Over time, as shown in FIG. 50c, the epithelium sheet 1210 will grow and adhere to the top layer 1230 of the stroma 1240, as well as the mask 1200 depending, of course, on the composition of the mask 1200. As needed, a contact lens may be placed over the incised cornea to protect the mask.

Figure 51A:
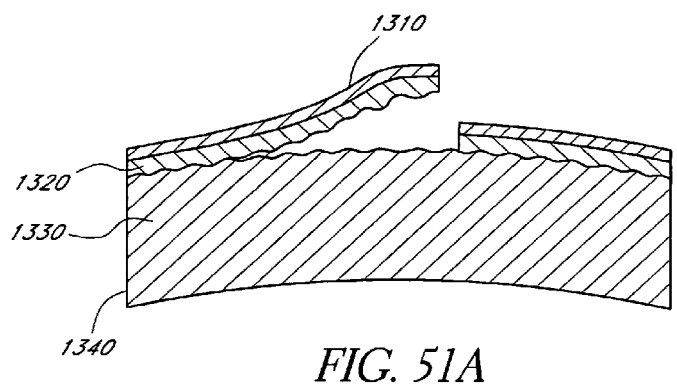
FIGS. 51A-51C show a mask, similar to those described herein, inserted beneath a Bowman's membrane of a cornea.
Figure 51B:
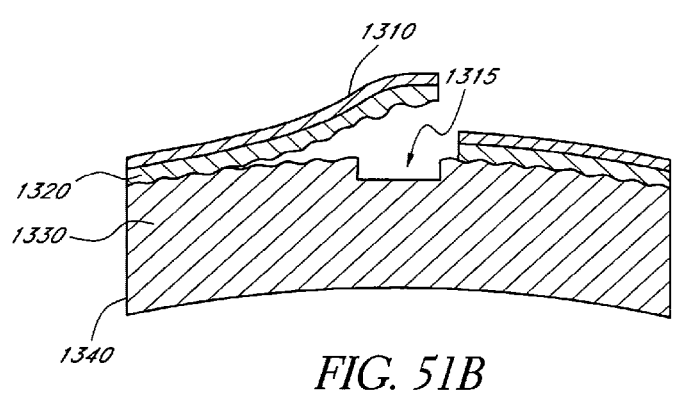
Figure 51C:
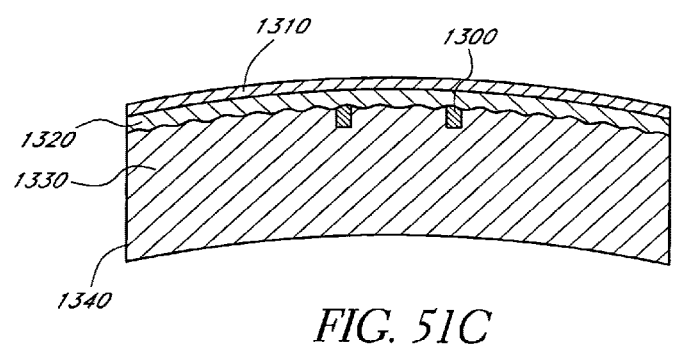

FIGS. 51a through 51c show a mask 1300 inserted beneath a Bowman's membrane 1320 of an eye. In this embodiment, as shown in FIG. 51a, the surgeon first hinges open the Bowman's membrane 1320. Then, as shown in FIG. 51b, the surgeon creates a depression 1315 in a top layer 1300 of a stroma 1340 corresponding to the visual axis of the eye. The visual axis of the eye may be located as described above and may be marked by any suitable technique, for example using a visible ocular feature or a technique employing patient input. The depression 1315 should be of sufficient depth and width to accommodate the mask 1300. Then, the mask 1300 is placed in the depression 1315. Because the depression 1315 is located in a position to correspond to the visual axis of the patient's eye, the central axis of the pinhole aperture of the mask 1300 will be substantially collinear with the visual axis of the eye. This will provide the greatest improvement in vision possible with the mask 1300. Last, the Bowman's membrane 1320 is placed over the mask 1300. Over time, as shown in FIG. 51c, the epithelium sheet 1310 will grow over the incised area of the Bowman's membrane 1320. As needed, a contact lens may be placed over the incised cornea to protect the mask.

In another embodiment, a mask of sufficient thinness, i.e., less than substantially 20 microns, may be placed underneath epithelium sheet 1210. In another embodiment, an optic mark having a thickness less than about 20 microns may be placed beneath Bowman's membrane 1320 without creating a depression in the top layer of the stroma.

In an alternate method for surgically implanting a mask in the eye of a patient, the mask may be threaded into a channel created in the top layer of the stroma. In this method, a curved channeling tool creates a channel in the top layer of the stroma, the channel being in a plane parallel to the surface of the cornea. The channel is formed in a position corresponding to the visual axis of the eye. The channeling tool either pierces the surface of the cornea or, in the alternative, is inserted via a small superficial radial incision. In the alternative, a laser focusing an ablative beam may create the channel in the top layer of the stroma. In this embodiment, the mask may be a single segment with a break, or it may be two or more segments. In any event, the mask in this embodiment is positioned in the channel and is thereby located so that the central axis of the pinhole aperture formed by the mask is substantially collinear with the patient's visual axis to provide the greatest improvement in the patient's depth of focus.

In another alternate method for surgically implanting a mask in the eye of a patient, the mask may be injected into the top layer of the stroma. In this embodiment, an injection tool with a stop penetrates the surface of the cornea to the specified depth. For example, the injection tool may be a ring of needles capable of producing a mask with a single injection. In the alternative, a channel may first be created in the top layer of the stroma in a position corresponding to the visual axis of the patient. Then, the injector tool may inject the mask into the channel. In this embodiment, the mask may be a pigment, or it may be pieces of pigmented material suspended in a bio-compatible medium. The pigment material may be made of a polymer or, in the alternative, made of a suture material. In any event, the mask injected into the channel is thereby positioned so that the central axis of the pinhole aperture formed by the pigment material is substantially collinear with the visual axis of the patient.

In another method for surgically implanting a mask in the eye of a patient, the mask may be placed beneath the corneal flap created during keratectomy, when the outermost 20% of the cornea is hinged open. As with the implantation methods discussed above, a mask placed beneath the corneal flap created during keratectomy should be substantially aligned with the patient's visual axis, as discussed above, for greatest effect.

In another method for surgically implanting a mask in the eye of a patient, the mask may be aligned with the patient's visual axis and placed in a pocket created in the cornea's stroma.

Further details concerning alignment apparatuses are disclosed in U.S. Provisional Application Ser. No. 43/479,129, filed Jun. 17, 2003, incorporated by reference herein in its entirety.

VI. Further Methods of Treating a Patient

As discussed above in, various techniques are particularly suited for treating a patient by applying masks such as those disclosed herein to an eye. For example, in some techniques, a visual cue in the form of a projected image for a surgeon is provided during a procedure for applying a mask. In addition, some techniques for treating a patient involve positioning an implant with the aid of a marked reference point. These methods are illustrated by FIGS. 52-53B.

In one method, a patient is treated by placing an implant 1400 in a cornea 1404. A corneal flap 1408 is lifted to expose a surface in the cornea 1404 (e.g., an intracorneal surface). Any suitable tool or technique may be used to lift the corneal flap 1408 to expose a surface in the cornea 1404. For example, a blade (e.g., a microkeratome), a laser or an electrosurgical tool could be used to form a corneal flap. A reference point 1412 on the cornea 1404 is identified. The reference point 1412 thereafter is marked in one technique, as discussed further below. The implant 1400 is positioned on the intracorneal surface. In one embodiment, the flap 1408 is then closed to cover at least a portion of the implant 1400.

The surface of the cornea that is exposed is a stromal surface in one technique. The stromal surface may be on the corneal flap 1408 or on an exposed surface from which the corneal flap 1408 is removed.

The reference point 1412 may be identified in any suitable manner. For example, the alignment devices and methods described above may be used to identify the reference point 1412. In one technique, identifying the reference point 1412 involves illuminating a light spot (e.g., a spot of light formed by all or a discrete portion of radiant energy corresponding to visible light, e.g., red light). As discussed above, the identifying of a reference point may further include placing liquid (e.g., a fluorescein dye or other dye) on the intracorneal surface. Preferably, identifying the reference point 1412 involves alignment using any of the techniques described herein.

As discussed above, various techniques may be used to mark an identified reference point. In one technique the reference point is marked by applying a dye to the cornea or otherwise spreading a material with known reflective properties onto the cornea. As discussed above, the dye may be a substance that interacts with radiant energy to increase the visibility of a marking target or other visual cue. The reference point may be marked by a dye with any suitable tool. The tool is configured so that it bites into a corneal layer, e.g., an anterior layer of the epithelium, and delivers a thin ink line into the corneal layer in one embodiment. The tool may be made sharp to bite into the epithelium. In one application, the tool is configured to deliver the dye as discussed above upon being lightly pressed against the eye. This arrangement is advantageous in that it does not form a larger impression in the eye. In another technique, the reference point may be marked by making an impression (e.g., a physical depression) on a surface of the cornea with or without additional delivery of a dye. In another technique, the reference point may be marked by illuminating a light or other source of radiant energy, e.g., a marking target illuminator and projecting that light onto the cornea (e.g., by projecting a marking target).

Any of the foregoing techniques for marking a reference point may be combined with techniques that make a mark that indicates the location of an axis of the eye, e.g., the visual axis or line-of-sight of the eye. In one technique, a mark indicates the approximate intersection of the visual axis and a surface of the cornea. In another technique, a mark is made approximately radially symmetrically disposed about the intersection of the visual axis and a surface of the cornea.

As discussed above, some techniques involve making a mark on an intracorneal surface. The mark may be made by any suitable technique. In one technique a mark is made by pressing an implement against the intracorneal surface. The implement may form a depression that has a size and shape that facilitate placement of a mask. For example, in one form the implement is configured to form a circular ring (e.g., a thin line of dye, or a physical depression, or both) with a diameter that is slightly larger than the outer diameter of a mask to be implanted. The circular ring can be formed to have a diameter between about 4 mm and about 5 mm. The intracorneal surface is on the corneal flap 1408 in one technique. In another technique, the intracorneal surface is on an exposed surface of the cornea from which the flap was removed. This exposed surface is sometimes referred to as a tissue bed.

In another technique, the corneal flap 1408 is lifted and thereafter is laid on an adjacent surface 1416 of the cornea 1404. In another technique, the corneal flap 1408 is laid on a removable support 1420, such as a sponge. In one technique, the removable support has a surface 1424 that is configured to maintain the native curvature of the corneal flap 1408.

FIG. 52 shows that the marked reference point 1412 is helpful in positioning an implant on an intracorneal surface. In particular, the marked reference point 1412 enables the implant to be positioned with respect to the visual axis of the eye. In the illustrated embodiment, the implant 1400 is positioned so that a centerline of the implant, indicated as $M_{CL}$, extends through the marked reference point 1412.

FIG. 52A illustrates another technique wherein a reference 1412' is a ring or other two dimensional mark. In such a case, the implant 1400 may be placed so that an outer edge of the implant and the ring correspond, e.g., such that the ring and the implant 1400 share the same or substantially the same center. Preferably, the ring and the implant 1400 are aligned so that the centerline of the implant $M_{CL}$ is on the line of sight of the eye, as discussed above. The ring is shown in dashed lines because in the illustrated technique, it is formed on the anterior surface of the corneal flap 1408.

In one technique, the corneal flap 1408 is closed by returning the corneal flap 1408 to the cornea 1404 with the implant 1400 on the corneal flap 1408. In another technique, the corneal flap 1408 is closed by returning the corneal flap 1408 to the cornea 1404 over the implant 1400, which previously was placed on the tissue bed (the exposed intracorneal surface).

When the intracorneal surface is a stromal surface, the implant 1400 is placed on the stromal surface. At least a portion of the implant 1400 is covered. In some techniques, the implant 1400 is covered by returning a flap with the implant 1400 thereon to the cornea 1404 to cover the stromal surface. In one technique, the stromal surface is exposed by lifting an epithelial layer to expose stroma. In another technique, the stromal surface is exposed by removing an epithelial layer to expose stroma. In some techniques, an additional step of replacing the epithelial layer to at least partially cover the implant 1400 is performed.

After the flap 1408 is closed to cover at least a portion of the implant 1400, the implant 1400 may be repositioned to some extent in some applications. In one technique, pressure is applied to the implant 1400 to move the implant into alignment with the reference point 1412. The pressure may be applied to the anterior surface of the cornea 1404 proximate an edge of the implant 1400 (e.g., directly above, above and outside a projection of the outer periphery of the implant 1400, or above and inside a projection of the outer periphery of the implant 1400). This may cause the implant to move slightly away from the edge proximate which pressure is applied. In another technique, pressure is applied directly to the implant. The implant 1400 may be repositioned in this manner if the reference point 1412 was marked on the flap 1408 or if the reference point 1412 was marked on the tissue bed. Preferably, pushing is accomplished by inserting a thin tool under the flap or into the pocket and directly moving the inlay.

FIG. 53 shows that a patient may also be treated by a method that positions an implant 1500 in a cornea 1504, e.g., in a corneal pocket 1508. Any suitable tool or technique may be used to create or form the corneal pocket 1508. For example, a blade (e.g., a microkeratome), a laser, or an electrosurgical tool could be used to create or form a pocket in the cornea 1504. A reference point 1512 is identified on the cornea 1504. The reference point may be identified by any suitable technique, such as those discussed herein. The reference point 1512 is marked by any suitable technique, such as those discussed herein. The corneal pocket 1508 is created to expose an intracorneal surface 1516. The corneal pocket 1508 may be created at any suitable depth, for example at a depth within a range of from about 50 microns to about 300 microns from the anterior surface of the cornea 1504. The implant 1500 is positioned on the intracorneal surface 1516. The marked reference point 1512 is helpful in positioning the implant 1500 on the intracorneal surface 1516. The marked reference point 1512 enables the implant 1500 to be positioned with respect to the visual axis of the eye, as discussed above. In the illustrated embodiment, the implant 1500 is positioned so that a centerline $M_{CL}$ of the implant 1500 extends through or adjacent to the marked reference point 1512.

FIG. 53A illustrates another technique wherein a reference 1512' is a ring or other two dimensional mark. In such case, the implant 1500 may be placed so that an outer edge of the implant and the ring correspond, e.g., such that the ring and the implant 1500 share the same or substantially the same center. Preferably, the ring and the implant 1500 are aligned so that the centerline of the implant $M_{CL}$ is on the line of sight of the eye, as discussed above. The ring is shown in solid lines because in the illustrated embodiment, it is formed on the anterior surface of the cornea 1504 above the pocket 1508.

After the implant 1500 is positioned in the pocket 1508, the implant 1500 may be repositioned to some extent in some applications. In one technique, pressure is applied to the implant 1500 to move the implant into alignment with the reference point 1512. The pressure may be applied to the anterior surface of the cornea 1504 proximate an edge of the implant 1500 (e.g., directly above, above and outside a projection of the outer periphery of the implant 1500, or above and inside a projection of the outer periphery of the implant 1500). This may cause the implant 1500 to move slightly away from the edge at which pressure is applied. In another technique, pressure is applied directly to the implant 1500.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the devices may be made that achieve or optimize one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. An ophthalmic device, comprising:
    a mask configured to increase the depth of focus of the patient and comprising a highly fluorinated polymeric material in which the number of carbon-fluorine bonds equals or exceeds the number of carbon-hydrogen bonds in the highly fluorinated polymeric material,
    the mask further comprising an aperture configured to transmit light and a portion configured to be substantially opaque to visible light and to surround at least a portion of the aperture; and
    a plurality of light transmissive structures in the substantially opaque portion configured to reduce the tendency of visible light that passes through the light transmissive structures to produce visible diffraction patterns.

2. The ophthalmic device of claim 1, wherein at least a portion of the mask comprises a coating comprising the highly fluorinated polymeric material.

3. The ophthalmic device of claim 1, wherein the coating is at least on an anterior surface of the mask.

4. The ophthalmic device of claim 1, wherein the highly fluorinated polymeric material comprises polyvinylidene fluoride (PVDF).

5. The ophthalmic device of claim 1, wherein the mask comprises a second polymer different from the highly fluorinated polymeric material.

6. The ophthalmic device of claim 5, wherein the second polymer comprises one or more generally UV transparent or reflective polymers.

7. The ophthalmic device of claim 5, wherein the mask comprises a blend of the highly fluorinated polymeric material and the second polymer.

8. The ophthalmic device of claim 1, wherein the substantially opaque portion comprises an opacification agent selected from the group consisting of organic dyes, organic pigments, inorganic dyes, and inorganic pigments.

9. The ophthalmic device of claim 8, wherein the opacification agent is applied to one or more surfaces of the mask.

10. The ophthalmic device of claim 1, wherein the substantially opaque portion comprises carbon.

11. The ophthalmic device of claim 1, wherein highly fluorinated polymeric material comprises at least one of polytetrafluoroethylene, polyvinylidene fluoride, poly-1,1,2-trifluoroethylene, perfluoroalkoxyethylene, fluorinated polyimide, and fluorinated acrylate.

12. The ophthalmic device of claim 1, wherein highly fluorinated polymeric material comprises one or more of the following monomer units: tetrafluoroethylene —($CF_2$-$CF_2$)—, vinylidene fluoride —($CF_2$—$CH_2$)—, 1,1,2-trifluoroethylene —($CF_2$—CHF)—, hexafluoropropene —(CF($CF_3$)—$CF_2$)—, and vinyl fluoride —($CH_2$—CHF)—.

13. The ophthalmic device of claim 1, wherein the highly fluorinated polymeric material comprises one or more monomers that comprise at least one of oxygen and chlorine.

14. The ophthalmic device of claim 1, wherein the aperture has a dimension generally transverse to the optical axis, the dimension being about 2.2 millimeters or less.

15. The ophthalmic device of claim 1, wherein the mask has a thickness between an anterior surface and a posterior surfaces of about 20 microns or less.

16. The ophthalmic device of claim 1, wherein the mask comprises about 80-100% of the highly fluorinated polymeric material.

17. The ophthalmic device of claim 1, wherein the mask comprises about 40-60% of the highly fluorinated polymeric material.

18. A corneal inlay, comprising:
    an anterior surface configured to reside adjacent a first corneal layer;
    a posterior surface configured to reside adjacent a second corneal layer;
    an aperture configured to transmit light therethrough and a non-transmissive portion disposed about the aperture; and a plurality of nutrient flow paths extending at least partially between the anterior surface and the posterior surface, at least some of the nutrient flow paths having a hole entrance disposed on one of the anterior surface and the posterior surface and a hole exit disposed on one of the anterior surface and the posterior surface different from the hole entrance wherein the hole entrance and hole exit at least partially overlap to permit transmission of light, the plurality of flow paths being configured to substantially eliminate diffraction patterns visible to the patient due to the transmission of visible light through the at least some of the nutrient flow paths;

wherein the corneal inlay comprises a highly fluorinated polymeric material in which the number of carbon-fluorine bonds equals or exceeds the number of carbon-hydrogen bonds.

19. An ophthalmic device, comprising:
a mask configured to increase the depth of focus of the patient and comprising a fluorinated polymer having one or more carbon-fluorine bonds,
the mask further comprising an aperture configured to transmit light and a portion configured to be substantially opaque to visible light and to surround at least a portion of the aperture; and
a plurality of light transmissive structures in the substantially opaque portion configured to reduce the tendency of visible light that passes through the light transmissive structures to produce visible diffraction patterns.

* * * * *

UNITED STATES PATENT AND TRADEMARK OFFICE
CERTIFICATE OF CORRECTION

PATENT NO. : 8,287,592 B2
APPLICATION NO. : 13/152550
DATED : October 16, 2012
INVENTOR(S) : Silvestrini Page 1 of 2

It is certified that error appears in the above-identified patent and that said Letters Patent is hereby corrected as shown below:

Title Page

Page 1 (item 63), Related U.S. Application Data at line 2, Change "Apr. 15, 2005," to --Apr. 14, 2005,--.

In column 2 (page 1 item 56) at line 17, Under Other Publications, change "Accomodation" to --Accommodation--.

In column 2 (page 4 item 56) at line 48, Under Other Publications, change "Opthalmology" to --Ophthalmology--.

In column 2 (page 4 item 56) at line 49, Under Other Publications, change "Accomodation" to --Accommodation--.

In column 2 (page 4 item 56) at line 75, Under Other Publications, change "Stenipeic" to --Stenopeic--.

In column 1 (page 5 item 56) at line 9, Under Other Publications, change "accomodation." to --accommodation.--.

In column 1 (page 5 item 56) at line 56, Under Other Publications, change "Intracornel" to --Intracorneal--.

In column 2 (page 5 item 56) at line 23, Under Other Publications, change "intracorneallens" to --intracorneal lens--.

In column 2 (page 5 item 56) at line 32, Under Other Publications, change "Sugery" to --Surgery--.

In column 2 (page 5 item 56) at line 51, Under Other Publications, change "The. Wolgenuth, Lonny.Business" to --The Wolgemuth, Lonny Business--.

In column 2 (page 5 item 56) at line 52, Under Other Publications, change "Manfacturing" to --Manufacturing--.

Signed and Sealed this
Seventh Day of May, 2013

Teresa Stanek Rea
*Acting Director of the United States Patent and Trademark Office*

In column 2 (page 5 item 56) at line 70, Under Other Publications, change "Keratoplosty:" to -- Keratoplasty:--.

In column 2 (page 5 item 56) at lines 70-71, Under Other Publications, change "Cyropreservation,"" to --Cryopreservation."--.

In column 1 (page 6 item 56) at line 11, Under Other Publications, change "Hydrophopic" to --Hydrophobic--.

In column 1 (page 6 item 56) at line 12, Under Other Publications, change "Absorving" to --Absorbing--.

In column 1 (page 6 item 56) at line 19, Under Other Publications, change "Hydrophopic" to --Hydrophobic--.

In column 2 (page 6 item 56) at line 25, Under Other Publications, change "flouride" to --fluoride--.

In the Specifications:

In column 5 at line 28, Change "presbyotic" to --presbyopic--.
In column 5 at line 33, Change "presbyotic" to --presbyopic--.
In column 6 at line 28, Change "34f. FIG. 13" to --34f FIG. 13--.
In column 12 at line 42, Change "ilminite," to --ilmenite,--.
In column 13 at line 28, Change "Visibile" to --Visible--.